United States Patent [19]

Uraneck et al.

[11] 4,297,451

[45] Oct. 27, 1981

[54] DIENYLLITHIUM INITIATED POLYMERS

[75] Inventors: Carl A. Uraneck; John E. Burleigh; Paul W. Solomon, all of Bartlesville, Okla.

[73] Assignee: Phillips Petroleum Company, Bartlesville, Okla.

[21] Appl. No.: 55,868

[22] Filed: Jul. 10, 1979

[51] Int. Cl.$^3$ .............................................. C08L 49/00
[52] U.S. Cl. .................................. 525/366; 525/242; 525/250; 525/271; 525/292; 525/313; 525/333; 525/335; 525/355; 526/124; 526/123
[58] Field of Search ............... 525/250, 271, 366, 333, 525/335, 355, 292, 313, 242; 526/124, 123

[56] References Cited

U.S. PATENT DOCUMENTS

| | | | |
|---|---|---|---|
| 3,235,626 | 2/1966 | Waack | 525/250 |
| 3,265,765 | 8/1966 | Holden et al. | 525/250 |
| 3,492,369 | 1/1970 | Naylor | 525/250 |
| 3,506,631 | 4/1970 | Halasa | 525/271 |
| 3,651,025 | 3/1972 | Bean et al. | 526/124 |
| 3,668,263 | 6/1972 | Morrison et al. | 526/124 |
| 3,670,054 | 6/1972 | De La Mare et al. | 525/271 |
| 3,776,964 | 12/1973 | Morrison et al. | 526/124 |
| 3,786,116 | 1/1974 | Milkovich et al. | 525/250 |
| 3,832,423 | 8/1974 | Milkovich et al. | 525/250 |
| 3,851,000 | 11/1974 | Selman | 526/124 |
| 3,884,889 | 5/1975 | Hsieh | 526/124 |
| 3,931,126 | 1/1976 | Naylor | 526/124 |
| 3,976,628 | 8/1976 | Halasa et al. | 525/250 |

OTHER PUBLICATIONS

Furukawa et al., *Ionic Polymerization*, pp. 367–387, (1976), Marcel Dekker Inc., New York, N.Y.
Jalics, *J. Poly. Sci., Poly. Chem. Ed.*, vol. 15, (1977), 1527.
Newcomb et al., *J. Org. Chem.*, vol. 39, No. 2, (1974), 232–236.
Newcomb et al., *J. Poly. Sci.*, Part B, (*Polymer Letters*), vol. 10, (1972), 17–22.
Kern et al., *J. Appl'd. Poly. Sci.*, vol. 16, (1972), 3123–3131.
Yasuda et al., *Tetrahedron Letters*, No. 27, (1973), 2443–2446.
Yasuda et al., *Macromolecules*, vol. 7, No. 1, (1974), 143–145.
Anderson et al., *J. Appl'd. Poly. Sci.*, vol. 16, (1972), 3133–3144.
Bi et al., *International Rubber Conference*, ("Rubbercon '77"), Brighton, England, 1, (1977), 11-1 thru 11-9.
Bates et al., *Tetrahedron Letters*, No. 3, (1967), pp. 199–204.

*Primary Examiner*—Harold D. Anderson

[57] ABSTRACT

Polymers are prepared using dienyllithium initiators, a reaction product of organolithium with a 1,4-diolefin, to polymerize olefinically unsaturated monomers such as conjugated dienes under solution polymerization conditions to provide unsaturated polymers, branched polymers, graft polymers, polymers prepared by sequential polymerization, and coupled polymers.

57 Claims, No Drawings

DIENYLLITHIUM INITIATED POLYMERS

FIELD OF THE INVENTION

The invention pertains to polymers containing terminal groups having multiple unsaturation. The invention also pertains to branched polymers prepared by self polymerization of living polymers having conjugated dienyl terminal groups. In another aspect, the invention pertains to graft copolymers employing sequential addition of a second monomer to a living polymer having conjugated dienyl terminal groups. In a further aspect, the invention pertains to cross-linked high molecular weight polymers utilizing reinitiation of a preformed polymer having one or more conjugated dienyl terminal groups. In a still further aspect, the invention relates to coupled polymers.

BACKGROUND OF THE INVENTION

Solution polymerization of conjugated diene and other monomers with a variety of organolithium based initiators and various types of "termination" have been employed to place various active terminal groups on such polymers, such as hydroxy, and the like, for various curing purposes. Needed, however, has been some way to produce a polymer with more useful terminal groups to lead to improved properties, broader ranges of applications, particularly for superior vulcanizates.

BRIEF SUMMARY OF THE INVENTION

We have discovered that the use of what can be briefly termed dienyllithium initiators provides polymers and copolymers by solution polymerization methods which have unusual terminally reactive dienyl groups and which provide improved properties resulting in, for example, superior vulcanizates.

The polymers of our invention are prepared by initiating the polymerization of olefinically monounsaturated and diunsaturated organic monomers under solution polymerization conditions with a dienyllithium initiator. The resulting living polymer can be terminated with an agent containing an active hydrogen, can be coupled with various di- or polyfunctional coupling agents, terminated by capping with a compound which provides the polymer with a terminal group having conjugated unsaturation, can be maintained under conditions to provide self-polymerization of the living polymer, treated with a further reactive monomer to yield a graft polymer, further reacted with another portion of anionic initiator, or combination of these treatments.

DETAILED DESCRIPTION OF THE INVENTION

Dienyllithium Initiators

The dienyllithium initiators are prepared by reacting hydrocarbon 1,4-diolefins with hydrocarbon lithium compounds.

The hydrocarbon 1,4-diolefins can be cyclic or acyclic, and there does not presently appear to be a limitation on carbon atom range as far as operability is concerned. For convenient availability, those 1,4-olefins of 5 to 12 carbon atoms per molecule are presently preferred. Examples of such 1,4-diolefins include 1,4-pentadiene, 2-methyl-1,4-pentadiene, 3-methyl-1,4-pentadiene, 1,4-hexadiene, 1-methyl-1,4-cyclohexadiene, terpinolene, β-terpinene, γ-terpinene, and the like, alone, or in admixture.

The hydrocarbon lithium compounds employed in reaction with the 1,4-diolefins can be represented by the formula $R(Li)_x$, in which R is a hydrocarbon radical which can be a saturated aliphatic, saturated cycloaliphatic, aromatic, or combination radical, and x is an integer of 1 to 4. The R group has a valence equal to x. There does not presently appear to be a limitation as far as operability is concerned on the size of the R group, but for convenience and availability R preferably will contain 1 to 20 carbon atoms.

Examples of the hydrocarbon organolithium compounds include methyllithium, isopropyllithium, n-butyllithium, sec-butyllithium, tert-butyllithium, n-decyllithium, phenyllithium, naphthyllithium, 4-butyl-phenyllithium, p-tolyllithium, 4-phenyl-butyllithium, cyclohexyllithium, menthyllithium, 1,4-dilithiobutane, 1,20-dilithioeicosane, 1,4-dilithiocyclohexane, 1,5-dilithionaphthalene, 1,3,5-trilithiopentane, 1,2,4,6-tetralithiocyclohexane, and the like, alone or in admixture. Primary alkyllithiums, such as n-butyllithium, presently are preferred because of availability.

These dienyllithium initiators are prepared according to the general procedures described by R. B. Bates, D. W. Gosselink, and J. A. Kaczynski in *Tetrahedron Letters*, No. 3, 199–204 (1967). In general, this procedure involves the reaction of one or more of the 1,4-diolefins with at least one hydrocarbon organolithium at a reduced temperature in a solvent mixture of a saturated hydrocarbon/polar solvent such as hexane/tetrahydrofuran.

The ratio of organolithium compound to 1,4-diolefin normally is in the range of about 0.9:1 to 1:1 lithium equivalents per mole of 1,4-diolefin. Preferred is the use of a slight excess of diene to assure complete conversion of all organolithium to dienyllithium.

The volume ratio of saturated hydrocarbon:polar solvent should predominate in hydrocarbon, such as about 20:1 to 2:1, preferably about 5:1 to 2:1, presently most preferably about 3:1. The amount of solvent used is that which is sufficient to keep the organolithium product essentially in solution.

The saturated hydrocarbon is selected from one or more of the aliphatic hydrocarbons which are normally liquid, alone or in admixture. Examples of the hydrocarbons include n-pentane, n-hexane, n-heptane, cyclopentane, and cyclohexane, alone, or in admixture. Presently preferred is n-heptane.

The polar solvent component of the solvent admixture can be any one or more of the normally liquid ethers, such as in the range of 2 to 8 carbon atoms per molecule. Examples of the polar components include tetrahydrofuran, dimethyl ether, diethyl ether, and di-n-butyl ether, alone, or in admixture. Presently preferred is tetrahydrofuran.

The reaction between the 1,4-diolefin and the organolithium compound $R(Li)_x$ is considered to be a transmetalation reaction and is believed to occur as the reaction mixture is allowed to slowly warm. Thus, the reactants and solvent mixture must be admixed at a suitable convenient low temperature as reaction begins immediately, such as about −100° C. to 0° C., more preferably about −80° C. to −20° C., particularly such as about −78° C. The cooled admixture is then gradually warmed up to room temperature to as high as such as about 30° C. Concurrently, the reaction mixture usually separates into two layers. Where separation does occur, as is usual but not always, the top layer normally contains a minor amount of organolithium compound and polar solvent, in a major amount of hydrocarbon, while the bottom layer contains the dienyllithium initiator in a major amount of polar solvent and a minor amount of hydrocarbon.

For use as polymerization initiators, the dienyl layer is separated. The dienyllithium compounds do not require prior isolation or purification, and can be stored in the reaction or makeup solvent at a low temperature of such as about −10° C. for indefinite storage. A protective atmosphere such as nitrogen, argon, or helium, typically is used and is considered necessary.

The amount of the dienyl initiator used in the polymerization can vary over a wide range, dependent, of course, on the desired molecular weight of the polymer, monomer reactivity, etc. It generally will be within the range of about 0.1 to 75 gram milliequivalents of lithium per 100 grams by weight of monomer with a preferred range being about 0.5 to 20 milliequivalents, based on titrated value in the dienyllithium initiator.

Although we do not wish to be bound by theory, the dienyllithium compounds can be thought of as having charge delocalization over five carbon atoms, and as a consequence should be able to assume three conformations if the starting 1,4-diolefin is not alicyclic in nature, as shown in FIG. 1. by this same theory, alicyclic dienyllithium compounds would be restricted to only one conformation, the specific conformation depending on the location of the double bonds in the starting 1,4-diolefin, as also shown in FIG. 1:

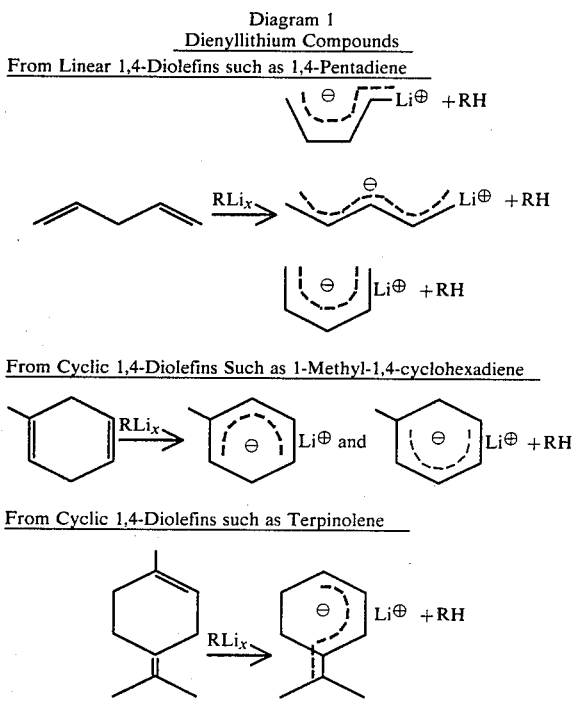

Diagram 1
Dienyllithium Compounds
From Linear 1,4-Diolefins such as 1,4-Pentadiene From Cyclic 1,4-Diolefins Such as 1-Methyl-1,4-cyclohexadiene From Cyclic 1,4-Diolefins such as Terpinolene In each of these conformations, the site of initiation, i.e. the carbon atom that becomes bound to the first monomer unit, can be at carbon numbers 1, 3, or 5. If attachment is at carbons 1 or 5, the resulting terminal diolefin on the polymer chain will have the desired conjugated unsaturation, whereas if attachment is at carbon number 3 of the initiating species, the resulting terminal diolefin will be non-conjugated. These types of possible terminal unsaturation are believed to be as shown in FIG. 2:

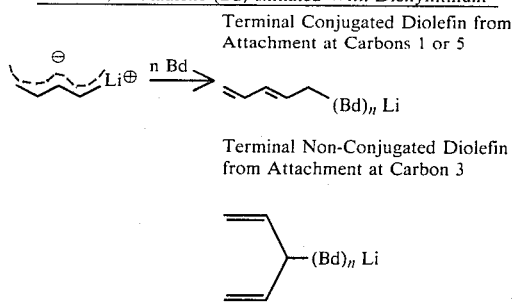

Diagram 2
Types of Possible Terminal Unsaturation on Polymer From 1,3-Butadiene (Bd) Initiated With Dienyllithium Terminal Conjugated Diolefin from Attachment at Carbons 1 or 5

Terminal Non-Conjugated Diolefin from Attachment at Carbon 3

The point of attachment for any given polymerization is believed to depend on the reagents and conditions of the reaction and the structure of the dienyllithium initiator. The statistical distribution of the types of terminal unsaturated functional group has not yet been accurately determined for the polymerizations of this invention. However, formation of polymer having the quantitative amount of conjugated dienyl-terminal groups based on the amount of dienyl initiator employed was not realized in these polymerizations. All that can be analyzed for is conjugated diene. Either the remainder of terminal groups are nonconjugated per attachment at carbon 3 (FIG. 2), or conjugated terminal group partially self-polymerized.

Monomers

Monomers capable of being polymerized using the dienyllithium initiators in the production of polymers in accordance with our invention are those olefinically monounsaturated and diunsaturated organic monomers polymerizable under solution polymerization conditions by the use of anionic initiators such as the organolithium initiators. Broadly, these monomers include the conjugated dienes, monovinylarenes, acrylates (acrylic and alkacrylic acid esters), vinyl pyridines, vinylidene halides, vinylquinolines, nitriles, N,N-disubstituted acrylamides, vinylfuran, N-vinyl carbazole. These monomers are polymerizable alone or in admixture with each other or by sequential polymerization, as is known in the art. Such monomers for availability generally contain in the range of 2 to 12 carbon atoms per molecule. Typical examples include 1,3-butadiene, isoprene, piperylene, styrene, 1-vinylnaphthalene, acrylonitrile, 2-vinylpyridine, 4-vinylpyridine, ethyl acrylate, methyl methacrylate, vinylidene chloride, and others as is well known in the art. Presently preferred are butadiene, isoprene, and styrene, preferred in conjugated diene/monovinylarene ratios of 100/0 to 0/100.

Polymers which can be prepared can include homopolymers, block copolymers, random copolymers, graft copolymers, and mixtures and combinations of these. Sequential polymerization techniques as described in the art are suitable.

Polymerization Conditions

Polymerization of the desired monomer or monomers can be accomplished by methods and techniques well known in the anionic solution polymerization arts.

The desired monomer or monomers can be contacted with the dienyllithium initiators in a hydrocarbon polymerization diluent. These hydrocarbon diluents include the paraffins, cycloparaffins, and aromatics, alone or in admixture, usually of 4 to 10 carbon atoms per molecule, including such as pentane, hexane, cyclohexane, n-heptane, benzene, toluene, and the like, alone or in admixture.

The polymerization step or steps can be conducted at polymerization temperatures generally suitable for anionic solution polymerization conditions. Typical suitable reaction conditions include temperatures in the range of about −40° to +100° C., presently preferably about +30° C. to +75° C., at any convenient pressure, usually sufficient to maintain substantially liquid phase conditions. Time of contact can be as convenient or desired, usually for several minutes to several hours, to produce a solution of living polymer, that is, polymer containing carbon-lithium bonds at one end of the polymer-molecules, thus capable of propagating further polymerization. The polymerization step normally is conducted to substantially complete polymerization (complete conversion).

Charging procedures, protection of monomers, diluents, initiators, finish polymer, and the like, against moisture and other materials which would tend to destroy the active lithium, is known in the art.

Treatment of the resulting living polymers with an active hydrogen-containing compound, such as isopropyl alcohol, gives a polymer which, as shown by ultraviolet spectroscopy, does contain at least some conjugated diene functional groups. However, the level of conjugated unsaturation is normally well below the maximum theoretical amount as discussed above. That a yield of a quantitative amount of terminal conjugated dienyl polymer is not obtained is thought to be at least partially due to the competition for the point of attachment of the initiator to the first monomer unit, as described previously.

There is a second competing reaction which is thought to also reduce the amount of conjugated dienyl functional group in the final polymer. This reaction involves a branching or self-coupling reaction occurring when the terminal living carbon-lithium bond of one polymer chain adds to the terminal conjugated dienyl functional group of a second polymer chain, as illustrated by FIG. 3:

Diagram 3

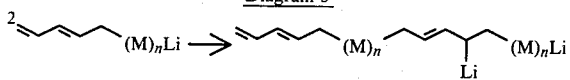

This competing reaction can lead to the formation of branched polymer if additional monomer is present (residual or added) to react with the carbon-lithium groups after this self-coupling occurs, and can also lead to cross-linked polymer if both carbon-lithium groups of the self-coupled product each react with another polymer chain having a terminal conjugated dienyl functional group.

Evidence that this self-coupling occurs lies in the observed increase in molecular weight and the broadening of the molecular weight distribution of the polymer, and in the reduction in the amount of conjugated unsaturation in the final polymer with longer polymerization times (deferred termination of living polymer).

Initiation polymerization of monovinylarenes with conjugated dienyllithium initiators results in a much faster rate and higher level of self-coupling, leading to branched and crosslinked poly(monovinylarene), than occurs when conjugated dienes are initiated with these dienyllithium initiators.

Sequential addition of a second monomer to living, self-coupled polymer leads to the formation of novel graft copolymers. These polymers are believed to be complex branched copolymers having sections which are typically block copolymeric in nature, and, in addition, the polymer has grafts of homopolymer and block copolymer at specific, limited sites on the polymeric backbone per FIG. 3.

At the end of polymerization at any of the above stages or aspects, the then living polymer can be terminated with any of the known active hydrogen-containing compounds.

Coupling

Alternatively to the treatment of the living polymer which contains a terminal conjugated dienyl functional group with an active hydrogen-containing compound, the living polymer can be coupled with di- or greater functionality coupling agents, or can be reacted with a compound which will provide a terminal group having conjugated unsaturation. The resulting polymers will be conjugated unsaturated telechelic polymers.

Coupling agents preferably are used because the resulting products exhibit an increase in Mooney viscosity as well as other desirable properties.

In our use of the term "coupling" as herein employed, the term is a broad generic term meaning the bringing together and joining by means of central coupling atom or coupling moiety, two or more of the living lithium-terminated polymer chains.

A wide variety of compounds as taught in the art for such purposes can be employed. Among the suitable coupling agents are the multivinylaromatic compounds, multiepoxides, multiisocyanates, multiimines, multialdehydes, multiketones, multihalides, multianhydrides, multiesters which include the esters of polyalcohols with monocarboxylic acids, as well as the diesters which are esters of monohydric alcohols with dicarboxylic acids, combination group agents, carbon monoxide, carbon dioxide, sulfur halides, the halogens, and the like.

Examples of suitable multivinylaromatic compounds include divinylbenzene, 1,2,4-trivinylbenzene, 1,3-divinylnaphthalene, 1,8-divinylnaphthalene, 1,3,5-trivinylnaphthalene, 2,4-divinylbiphenyl, and the like. The divinylaromatic hydrocarbons are preferred, particularly divinylbenzene in either its ortho, meta, or para isomer. Commercial divinylbenzene which is a mixture of the three isomers and other compounds is satisfactory.

While multiepoxides in general can be used, those which are liquid are more readily handled and form a relatively small nucleus for the coupled polymer. Convenient among the multiepoxides are the epoxidized hydrocarbon polymers such as epoxidized liquid polybutadiene and the epoxidized vegetable oils such as epoxidized soybean oil and epoxidized linseed oil. Other epoxy compounds such as 1,2; 5,6; 9,10-triepoxydecane, and the like, also can be used.

Examples of suitable multiisocyanates include benzene-1,2,4-triisocyanate, naphthalene-1,2,5,7-tetraisocyanate, and the like. Convenient is a commercially available product known as PAPI-1, a polyarylpolyisocyanate having an average of 3 isocyanate groups per molecule and an average molecular weight of about 380. Such a compound can be visualized as a series of isocyanate-substituted benzene rings joined through methylene linkages.

The multiimines, also known as multiaziridinyl compounds, preferably are those containing 3 or more aziridine rings per molecule. Examples include the triaziridinyl phosphine oxides or sulfides such as tri(1-aziridinyl)phosphine oxide, tri(2-methyl-1-aziridinyl)phosphine oxide, tri(2-ethyl-3-decyl-1-aziridinyl)phosphine sulfide, and the like.

The multialdehydes are represented by compounds such as 1,4,7-naphthalenetricarboxaldehyde, 1,7,9-anthracenetricarboxaldehyde, 1,1,5-pentanetricarboxaldehyde, and similar multialdehyde-containing aliphatic and aromatic compounds.

The multiketones are represented by compounds such as 1,4,9,10-anthracenetetrone, 2,3-diacetonylcyclohexanone, and the like.

Examples of the multianhydrides include pyromellitic dianhydride, styrene-maleic anhydride copolymers, and the like.

Examples of the multiesters include diethyladipate, triethylcitrate, 1,3,5-tricarbethoxybenzene, fatty acid esters of glycerol, and the like.

Among the multihalides, we presently prefer the silicon tetrahalides such as silicon tetrachloride, silicon tetrabromide, and silicon tetraiodide, and the trihalosilanes such as trifluorosilane, trichlorosilane, trichloroethylsilane, tribromobenzylsilane, and the like. Also preferred are the multihalogen-substituted hydrocarbons, such as 1,3,5-tri(bromomethyl)benzene, 2,5,6,9-tetrachloro-3,7-decadiene, and the like, in which the halogen is attached to a carbon atom which is alpha to an activating group such as an ether linkage, a carbonyl group, or a carbon-to-carbon double bond. Substituents inert with respect to lithium atoms in the terminally reactive polymer can also be present in the active halogen-containing compounds. Alternatively, other suitable reactive groups different from the halogen as described above can be present.

In addition to the silicon multihalides as described hereinabove, other metal multihalides, particularly those of tin, lead, or germanium, also can be readily employed as coupling and branching agents. Silicon and other metal multialkoxides, such as silicon tetraethoxide, are also suitable.

Examples of compounds containing more than one type of functional group include 1,3-dichloro-2-propanone, 2,2-dibromo-3-decanone, 3,5,5-trifluoro-4-octanone, 2,4-dibromo-3-pentanone, 1,2; 4,5-diepoxy-3-pentanone, 1,2; 4,5-diepoxy-3-hexanone, 1,2; 11,12-diepoxy-8-pentadecanone, 1,3; 18,19-diepoxy-7,14-eicosanedione, and the like.

Difunctional coupling agents can be employed where a linear polymer rather than a branched polymer is desired.

Broadly, and exemplarily, a range of about 0.01 to 4.5 milliequivalents of coupling agent are employed per 100 grams of monomer, presently preferred about 0.01 to 1.5 to obtain the desired Mooney viscosity. One equivalent of treating agent per equivalent of lithium is considered optimum amount for maximum branching, if this result is desired in the production line. The coupling agent can be added in hydrocarbon solution, e.g., in cyclohexane, to the polymerization admixture with suitable mixing for distribution and reaction.

Termination of Living Polymer With Unsaturated Compounds

Other suitable compounds that can be reacted with the living dienyllithium initiated (dienyl group terminated) polymers to provide a conjugated unsaturated terminal group include linear and cyclic conjugated unsaturated compounds which may also contain another reactive group capable of reacting with the lithium on the polymer. This is another method of forming polymer having telechelic conjugated diene groups. These compounds include alicyclic conjugated trienes and tetraenes having the structures

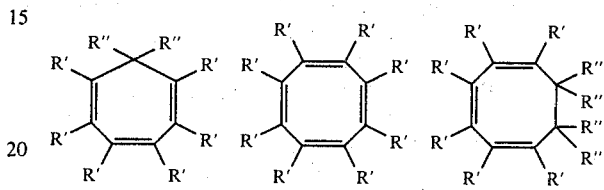

and linear conjugated dienes of the general structure

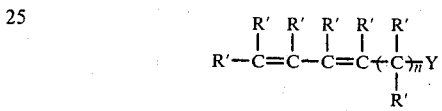

wherein R' is hydrogen or alkyl such that the total number of carbon atoms in the molecule does not exceed about 20, R" is R' or halogen with the stipulation that only one R" can be halogen; n is an integer having a value of 1 to 6; and Y is a functional group which will react readily with the lithium on the polymer, such as a halogen. Examples of suitable compounds for providing a terminal conjugated unsaturated functional group to the polymer include 1,3,5-cycloheptatriene, cyclooctatetraene, 5-chloro-1,3-pentadiene, 7-chloro-1,3,5-cycloheptatriene, 7-bromo-1,3,5-cyclooctatriene, 7-chloro-1-methyl-1,3,5-cycloheptatriene, and the like.

These compounds are normally added at a level to provide one mole of conjugated unsaturated compound per equivalent of lithium initiator employed in the polymerization. The conditions employed can be those previously described for coupling agents.

Termination

If the reaction of the living polymer with the unsaturated compounds or coupling agents results in a polymer which still retains lithium, such as for example when 1,3,5-cycloheptatriene or esters or divinylbenzene is employed, the polymer is shortstopped or terminated with at least an equivalent amount of an active hydrogen containing compound per equivalent of lithium. This is, of course, not necessary when the reaction between the living polymer and the conjugated unsaturated compound or the coupling agent is a substitution reaction wherein the lithium is removed from the living polymer, as, for example, lithium halide, when such as silicon tetrachloride, or 5-chloro-1,3-pentadiene is the reacting reagent.

Reinitiation

Conjugated unsaturated telechelic or semitelechelic terminated polymers can be reinitiated using organolithium initiators of the structure $R(Li)_x$ as described previously. The polymerization of the conjugated unsaturated terminal groups results in the formation of polymacromer having a broad molecular weight distribution. Such polymers can become highly crosslinked, and their formation may be allowed to proceed to a gelled product. Optionally, a monomer as previously described can be added along with the reinitiator to produce a polymacromer in admixture with polymer species of very broad molecular weight distribution.

Recovery

Generally, an antioxidant is added to the polymerization mixture just prior to recovery. The various polymers which can be prepared according to this invention can be recovered or isolated by any suitable means such as coagulation in alcohol, steam stripping, etc., followed by filtration and drying.

Utility

The polymers have a variety of useful applications depending on the particular polymer which is prepared, including use, for example, in tire treads, as adhesives, as impact resins, as loose gels of controlled structure, as mechanical rubber products, and the like.

EXAMPLES

The examples following are intended to assist one skilled in the art to a further understanding of the invention. Particular materials employed, ratios, relationships, species, and the like, are designed to be illustrative, and not limitative of the reasonable scope of the invention.

EXAMPLE I

The polymerization initiator pentadienyllithium was prepared by the general procedure described in R. B. Bates, D. W. Gosselink, and J. A. Kaczynski, *Tetrahedron Letters*, No. 3, 199–204 (1967).

A 475-ml. capacity Pyrex bottle was dried for about 15 hours at 90° C., and while still hot was flushed with dry nitrogen, capped with a perforated crown cap over a self-sealing rubber gasket, and pressured to about 0.17 MPa with dry nitrogen. After allowing to cool to room temperature, 200 ml. of 1.45 M n-butyllithium in n-heptane, and 80 ml. of dry tetrahydrofuran, were added to the bottle, and the bottle and contents then chilled to −78° C. in a Dry Ice-isopropanol bath. While maintaining the reaction mixture at this temperature, 32 ml. of 1,4-pentadiene was added, and after 15 minutes the bottle was transferred to a water-ice bath and maintained for 30 minutes. During the period of warm-up from −78° C. to 0° C. the solution separated into two layers, the lower, orange-yellow layer consisting essentially of pentadienyllithium in tetrahydrofuran. A 70 ml. portion of the bottom layer was diluted with 700 ml. of dry benzene and titrated using the disulfide technique described by C. A. Uraneck, J. E. Burleigh, and J. W. Cleary, *Anal. Chem.* 40 (2), 327 (1968). This solution was determined to be 0.2542 M in pentadienyllithium and was used as the initiator in the following polymerization.

Medium vinyl polybutadienes were prepared using the above pentadienyllithium as initiator. The polymer of Run 2 was terminated with alcohol; the polymer of Run 3 was terminated with 5-chloro-1,3-pentadiene; and the polymer of Run 4 was prepared by coupling the living polymer with α,α'-dichloro-p-xylene. As a control, in Run 1 a medium vinyl polybutadiene was prepared using n-butyllithium as initiator and terminated using isopropyl alcohol. In this as well as following recipes, where no coupling agent is shown in the recipe, termination was with alcohol.

The polymerizations were conducted employing essentially anhydrous reagents and conditions under an inert atmosphere (nitrogen) in 296 cc (10 oz.) beverage bottles equipped with perforated crown caps over self-sealing rubber gaskets. The bottles with their contents were agitated by tumbling in a constant temperature bath throughout the polymerization time. After the specified polymerization times, the antioxidant 2,6-di-t-butyl-4-methylphenol (two parts by weight per hundred parts of monomer) was added as a 10 weight percent solution in 80/20 (by volume) toluene/isopropyl alcohol, and the polymer then coagulated by adding isopropyl alcohol to the polymerization mixture. The addition of the antioxidant and the coagulation was conducted following Step I in Runs 1 and 2, and after Step II in Runs 3 and 4. Following coagulation, the polymers were collected by filtration and dried under reduced pressure at 60° C. Conversion of monomer to polymer was 90–100% for all runs. The medium vinyl polybutadiene polymers were prepared according to Recipe I:

| RECIPE I | | | | |
|---|---|---|---|---|
| | Run 1 (Control) | Run 2 | Run 3 | Run 4 |
| Step I | | | | |
| 1,3-Butadiene, p/w[a] | 100 | 100 | 100 | 100 |
| Cyclohexane, p/w | 804 | 792 | 793 | 811 |
| Tetrahydrofuran, p/w | 3.5 | 3.4 | 3.5 | 3.7 |
| Pentadienyllithium, mhm[b] | — | 0.99[c] | 0.92[d] | 1.81[e] |
| n-Butyllithium, mhm | 0.87[f] | — | — | — |
| Polym. temp., °C. | 50 | 50 | 50 | 50 |
| Polym. time, min. | 85 | 37 | 45 | 35 |
| Step II | | | | |
| 5-Chloro-1,3-pentadiene, mhm | — | — | 1.32[g] | — |
| α,α'-Dichloro-p-xylene, mhm | — | — | — | 0.76[h] |
| Reaction temp., °C. | — | — | 50 | 50 |
| Reaction time, min. | — | — | 25 | 20 |

[a] p/w = parts by weight.
[b] Millimoles per 100 grams of total monomers used in polymerization.
[c] Added as a 0.2486 M sol. in approx. 10/1 by vol. benzene/THF.
[d] Added as a 0.2133 M sol. in approx. 10/1 by vol. benzene/THF.
[e] Added as a 0.2542 M sol. in approx. 10/1 by vol. benzene/THF.
[f] Added as a 0.1098 M sol. in approx. 14/1 by vol. cyclohexane/n-heptane.
[g] Added as a 0.09 M sol. in cyclohexane.
[h] Added as a 0.138 M sol. in cyclohexane.

Physical properties of the medium vinyl polybutadiene polymers prepared according to Recipe I are shown in Table I:

TABLE I

| Physical Properties of Conjugated Dienyl Terminated Polymers | | | | |
|---|---|---|---|---|
| | Run 1 (Control) | Run 2 | Run 3 | Run 4 |
| ML-4[a] | 56 | 43 | 43.5 | 30 |
| Vinyl, %[b] | 50 | 44 | 44 | 40 |
| Trans, %[b] | 31 | 34 | 33 | 35 |
| I.V.[c] | 2.04 | 1.95 | 2.05 | 1.74 |
| $M_w$[d] | 248,000 | 219,000 | 244,000 | 228,000 |
| $M_n$[d] | 205,000 | 173,000 | 162,000 | 138,000 |
| H.I.[e] | 1.21 | 1.27 | 1.50 | 1.65 |
| Gel, wt. %[f] | 0 | 0 | 0 | 0 |

TABLE I-continued

| Physical Properties of Conjugated Dienyl Terminated Polymers | | | | |
|---|---|---|---|---|
| | Run 1 (Control) | Run 2 | Run 3 | Run 4 |
| Conj. unsat. wt. %[g] | 0 | 0.014 | 0.042 | 0.041 |

[a] Mooney Viscosity. ASTM D1646-74.
[b] Determined by infrared absorption spectroscopy.
[c] I.V. = inherent viscosity. Determined using the method described in U.S. Pat. No. 3,278,508, column 20, note a with the modification that the solution was not filtered through a sulfur absorption tube but rather a sample of the solution was filtered through a fritted glass filter stick of grade C porosity and pressured directly into the viscometer.
[d] $M_w$ = weight average molecular weight. $M_n$ = number average molecular weight. Determined using a gel permeation chromatography method as described by Gerard Kraus and C. J. Stacy, J. Poly. Sci.: Symposium No. 43, 329-343 (1973).
[e] H. I. = heterogeneity index. A measure of the molecular weight distribution and is the ratio of $M_w/M_n$. The higher the H. I., the broader the molecular weight distribution.
[f] Determined using the method described in U.S. Pat. No. 3,278,508, column 20, note b.
[g] Determined by UV absorption spectroscopy and calculated as weight percent 1,3-pentadienyl groups present in polymer.

The data in Table I demonstrate the effectiveness of pentadienyllithium as initiator for the polymerization of 1,3-butadiene. UV spectroscopy confirmed the presence of conjugated dienyl groups in the polymers, verifying that such groups can be incorporated into the polymer by the described procedure. The amount of conjugated unsaturation detected amounted to about 20-35% of the theoretical amount based on the amount of initiator and/or terminating agent employed, indicating that (A) reactions involving the conjugated dienyl group, i.e. self-polymerization, are occurring resulting in a loss of conjugated unsaturation, and/or (B) that the point of attachment of the initiator to the first monomer is such that a non-conjugated unsaturated terminal group is formed.

EXAMPLE II

The suitability for use in vulcanizable compounded stock of the medium vinyl polybutadiene polymers containing terminal conjugated unsaturation as prepared in Example I was studied.

Each of the polymers of Runs 1-5 inclusive was compounded according to the formulation given in Recipe II:

| Recipe II | |
|---|---|
| Ingredient | Parts by Weight |
| Rubber | 100 |
| Carbon Black[a] | 50 |
| Philrich ® 5[b] | 10 |
| Zinc oxide | 3 |
| Stearic acid | 2 |
| Flexamine G[c] | 1 |
| Sulfur | 1.75 |
| Santocure NS[d] | 0.8 |

[a] N330 type; Industry reference black number 4.
[b] a highly aromatic oil from Philips Petroleum Co.
[c] An antioxidant consisting of 65% of a complex diarylamine-ketone reaction product and 35% of commercial N,N'-diphenyl-p-phenylenediamine from Uniroyal Chemical.
[d] An accelerator having the structure N-t-butyl-2-benzothiazolesulfenamide from Monsanto.

All ingredients except the sulfur and the accelerator were mixed in a Midget Banbury for about 5 minutes at 110 rpm and dumped at a temperature of 154° to 160° C. Sulfur and accelerator were added on a second pass of the blend through the mixer, this second mixing being done at 80 rpm for 1.5 minutes, and the blend dumped at a temperature of 76° to 93° C. Additional mixing then was done for about 3 minutes at about 85° C. on a 3 inch roll mill. Each compounded rubber stock was cured at 150° C. for 30 minutes. Properties of each vulcanized compounded rubber are shown in Table II:

TABLE II

Properties of Compounded and Vulcanized Cojugated Dienyl Terminated Medium Vinyl Polybutadienes

| | Polymer Prepared In | | | |
|---|---|---|---|---|
| Property | Run 1 (Control) | Run 2 | Run 3 | Run 4 |
| ML-4 | 70 | 68 | 69 | 49 |
| Tensile (23° C.), MPa[a] | 16.5 | 14.1 | 18.0 | 16.5 |
| Elongation (23° C.), %[a] | 510 | 430 | 480 | 475 |
| 200% Modulus (23° C.) MPa[a] | 3.8 | 3.7 | 4.1 | 4.0 |
| 300% Modulus (23° C.) MPa[a] | 7.2 | 7.6 | 8.4 | 8.2 |
| Compression set, %[b] | 23.0 | 23.5 | 22.7 | 30.1 |
| ΔT, °C.[c] | 34.4 | 32.6 | 31.6 | 38.1 |
| Resilience, %[d] | 69.5 | 72.4 | 73.0 | 69.1 |
| Hardness, Shore A[e] | 55.5 | 56 | 55 | 53.5 |

[a] ASTM D412-75.
[b] ASTM D395-69. Method B was modified as follows: Compression devices were used with 0.325 inch spacers to give a static compression for the 0.5 inch pellet of 35%. The test was run for 2 hours at 100° C. plus a relaxation (after treatment) of 1 hour at 100° C.
[c] ASTM D623-69.
[d] ASTM D945-72. Test was modified in that specimen was a right circular cylinder 0.7 inch in diameter and 1 inch high.
[e] ASTM D2240-75.

These data demonstrate that polymers of Runs 2, 3, and 4 having terminal conjugated dienyl groups provide improved properties to vulcanized compounded stock compared to the control Run 1 without terminal conjugated dienyl groups. This improvement is evidenced by the reduced heat buildup (ΔT), resilience, and tensile strength of the vulcanized compounded rubber from Run 3; the reduced heat buildup and resilience of rubber from Run 2 (the unusually poor tensile strength appears to be a bad test point); and the relatively good values for the vulcanized rubber from Run 4 in view of its extremely low compounded Mooney viscosity (raw Mooney viscosity was significantly lower than for the other polymers—see Table I). It is believed that if the polymer from Run 4 had been prepared having Mooney viscosity equivalent to that of the Run 1 control, that then all the above-mentioned physical properties of rubber from Run 4 would be significantly superior to those of rubber from control Run 1.

EXAMPLE III

Dienyl initiators were prepared from each of 2-methyl-1,4-pentadiene, 3-methyl-1,4-pentadiene, terpinolene, and 1,4-hexadiene.

To a 475 ml. (1 pint) capacity Pyrex bottle (dried and capped as described in Example I) was added 150 ml. of 1.61 M n-butyllithium in n-heptane, and 60 ml. of dried tetrahydrofuran. After cooling this solution to −78° C., 20.8 grams of 2-methyl-1,4-pentadiene was added and the reaction mixture maintained at this temperature for 15 minutes. The mixture then was warmed to 0° C. and maintained for 45 minutes. During this time, a lower red layer separated. This layer (approximately 60 ml.) was removed and diluted with 607 ml. of toluene. Disulfide titration indicated this solution to be 0.246 M in 2-methylpentadienyllithium.

An organolithium compound was prepared from 3-methyl-1,4-pentadiene and n-butyllithium in a similar manner. Dilution of the lower layer of the reaction mixture with a 1/1 by volume tetrahydrofuran/cyclohexane mixture resulted in a bright red solution which was found by disulfide titration to be 0.849 M in 3-methylpentadienyllithium.

Terpinyllithium was prepared using 19 ml. of 1.61 M n-butyllithium, 8 ml. of tetrahydrofuran, and 3.72 grams of terpinolene, in like manner. However, there was no separation of the reaction mixture into two layers during the preparation of the terpinyllithium as had occurred during the preparation of all the earlier described dienyllithium initiators. Twenty-five ml. of the reaction mixture was diluted with 172 ml. of toluene to give a 0.1121 M solution of terpinyllithium.

1,3-Hexadienyllithium was prepared in similar manner using 100 ml. of 1.61 M n-butyllithium, 40 ml. of dry tetrahydrofuran, and 14 grams of 1,4-hexadiene. Separation of the reaction mixture into two layers did occur during its preparation, but at a slower rate than observed during the preparation of pentadienyllithium described in Example I. Furthermore, there was formation of some yellow precipitate. The lower deep red layer was diluted with toluene to give a solution 0.1284 M in hexadienyllithium.

Medium vinyl polybutadienes were prepared using the four initiators prepared described above and using the general procedure described in Example I according to Recipe III:

| Step I | RECIPE III Run 5 (Control) | Run 6 | Run 7 |
|---|---|---|---|
| 1,3-Butadiene, p/w | 100 | 100 | 100 |
| Cyclohexane, p/w | 810 | 804 | 800 |
| Tetrahydrofuran, p/w | 3.6 | 3.4 | 3.5 |
| n-Butyllithium, mhm[a] | 1.0 | — | — |
| 3-Methylpentadienyllithium, mhm[b] | — | 0.9 | — |
| 2-Methylpentadienyllithium, mhm[c] | — | — | 1.1 |
| Terpinyllithium, mhm[d] | — | — | — |
| Hexadienyllithium, mhm[e] | — | — | — |

| Step I | RECIPE III Run 5 (Control) | Run 6 | Run 7 |
|---|---|---|---|
| Polym. temp., °C. | 50 | 50 | 50 |
| Polym. time, hours | 1.7 | 0.8 | 0.8 |
| Step II | | | |
| α,α'-Dichloro-p-xylene, mhm[f] | — | — | — |
| Reaction temp., °C. | — | — | — |
| Reaction time, hours | — | — | — |

| Step I | Run 8 | Run 9 | Run 10 | Run 11 |
|---|---|---|---|---|
| 1,3-Butadiene, p/w | 100 | 100 | 100 | 100 |
| Cyclohexane, p/w | 800 | 810 | 778 | 803 |
| Tetrahydrofuran, p/w | 3.4 | 3.6 | 3.4 | 3.2 |
| n-Butyllithium, mhm[a] | — | — | — | — |
| 3-Methylpentadienyllithium, mhm[b] | — | — | — | — |
| 2-Methylpentadienyllithium, mhm[c] | 1.5 | — | — | — |
| Terpinyllithium, mhm[d] | — | 1.1 | — | — |
| Hexadienyllithium, mhm[e] | — | — | 1.0 | 1.5 |
| Polym. temp., °C. | 50 | 50 | 50 | 50 |
| Polym. time, hours | 0.9 | 0.8 | 0.8 | 1.0 |
| Step II | | | | |
| α,α'-Dichloro-p-xylene, mhm[f] | 0.76 | — | — | 0.75 |
| Reaction temp., °C. | 50 | — | — | 50 |
| Reaction time, hours | 0.8 | — | — | 0.6 |

[a] Added as a 0.1490 M sol. in approx. 10/1 by vol. cyclohexane/n-heptane.
[b] Added as a 0.849 M sol. in approx. 2/1 by vol. THF/cyclohexane.
[c] Added as a 0.246 M sol. in approx. 10/1 by vol. toluene/THF.
[d] Added as a 0.1121 M sol. in approx. 50/5/2 by vol. toluene/n-heptane/THF.
[e] Added as a 0.1121 M sol. in approx. 30/1 by vol. toluene/THF.
[f] Added as a 0.0876 M sol. in cyclohexane.

Physical properties of these polymers are shown in Table III-A:

TABLE III-A
Physical Properties of Medium Vinyl Polybutadienes Initiated with Dienyllithium Initiators

| Property | Run 5(Control) | Run 6 | Run 7 | Run 8 |
|---|---|---|---|---|
| ML-4 | 35 | 39 | 43 | 39 |
| Vinyl, % | 52 | 44 | 48 | 45 |
| Trans, % | 29 | 33 | 31 | 33 |
| I.V. | 1.79 | 1.66 | 1.87 | 1.81 |
| $M_w$ | 206,000 | 272,000 | 216,000 | 227,000 |
| $M_n$ | 185,000 | 222,000 | 220,000 | 181,000 |
| H.I. | 1.11 | 1.23 | 1.08 | 1.25 |
| Gel, wt. % | 0 | 0 | 0 | 0 |
| Conj. unsat., wt. % | 0.000 | 0.036 | 0.025 | 0.062 |

| Property | Run 9 | Run 10 | Run 11 |
|---|---|---|---|
| ML-4 | 39 | 39 | 38 |
| Vinyl, % | 47 | 48 | 45 |
| Trans, % | 32 | 30 | 34 |
| I.V. | 1.85 | 1.91 | 1.78 |
| $M_w$ | 225,000 | 230,000 | 247,000 |
| $M_n$ | 198,000 | 206,000 | 189,000 |
| H.I. | 1.14 | 1.12 | 1.30 |
| Gel, wt. % | 0 | 0 | 0 |
| Conj. unsat., wt. % | 0.004 | 0.021 | 0.055 |

These polymers were compounded according to Recipe II and the procedure described in Example II and evaluated as compounded and vulcanized stock. Properties of the compounded and vulcanized (45 minutes at 150° C.) rubber, are shown in Table III-B:

TABLE III - B
Properties of Compounded and Vulcanized Medium Vinyl Polybutadiene Prepared Using Dienyllithium Initiator

| Property | Polymer Prepared In | | |
| | Run 5(Control) | Run 6 | Run 7 |
|---|---|---|---|
| Initiator | NBL[a] | 3-MePdylLi[b] | 2-MePdylLi[c] |
| Coupled[f] | No | No | No |

TABLE III - B-continued

Properties of Compounded and Vulcanized Medium Vinyl Polybutadiene Prepared Using Dienyllithium Initiator

| | | | |
|---|---|---|---|
| Compounded ML-4 | 81 | 92 | 87 |
| Tensile (23° C.), MPa | 19.5 | 16.5 | 17.2 |
| Elongation (23° C.), % | 470 | 460 | 445 |
| 200% Modulus (23° C.), MPa | 5.3 | 4.2 | 4.8 |
| 300% Modulus (23° C.), MPa | 9.9 | 8.3 | 9.3 |
| Compression set, % | 12.7 | 11.8 | 12.8 |
| ΔT, °C. | 34.2 | 32.7 | 31.8 |
| Resilience, % | 65.1 | 70.0 | 67.9 |
| Hardness, shore A | 66 | 57 | 64 |

| | Polymer Prepared in | | | |
|---|---|---|---|---|
| Property | Run 8 | Run 9 | Run 10 | Run 11 |
| Initiator | 2-MePdylLi | TpLi[d] | HxLi[e] | HxLihu (e) |
| Coupled[f] | Yes | No | No | Yes |
| Compounded ML-4 | 87 | 87 | 94 | 74 |
| Tensile (23° C.), MPa | 17.6 | 17.2 | 18.5 | 17.4 |
| Elongation (23° C.), % | 415 | 410 | 450 | 415 |
| 200% Modulus (23° C.), MPa | 5.2 | 5.3 | 5.0 | 5.1 |
| 300% Modulus (23° C.), MPa | 10.3 | 10.3 | 9.8 | 10.2 |
| Compression set, % | 13.5 | 11.0 | 11.6 | 12.8 |
| ΔT, °C. | 32.2 | 33.7 | 32.6 | 33.5 |
| Resilience, % | 67.6 | 64.7 | 67.0 | 65.9 |
| Hardness, Shore A | 65 | 66 | 63 | 64 |

[a]n-Butyllithium
[b]3-Methylpentadienyllithium
[c]2-Methylpentadienyllithium
[d]Terpinyllithium
[e]Hexadienyllithium
[f]α,α'-Dichloro-p-xylene used as coupling agent.

These data demonstrate the reduced heat buildup (ΔT) and the generally improved resiliency for the dienyllithium initiated polymers of Runs 6–11 compared to the n-butyllithium-initiated polymer of Control Run 5. These superior properties of polymers of the invention Runs 6–11 are attributed to the terminal conjugated unsaturation which can be incorporated into the network structure of the vulcanizate and results in more efficient contribution of the polymer molecules to network strength.

EXAMPLE IV

Runs 12 through 15 demonstrate the loss in conjugated unsaturation as a function of polymerization time for polymers initiated with 2-methylpentadienyllithium and 3-methylpentadienyllithium.

Polymers containing high levels of unsaturated conjugation were prepared and the general procedures described in Example I. Where the polymers were prepared according to Recipe IV, and where no coupling agent is shown in the recipe, termination as by alcohol:

RECIPE IV

| | Run 12 | Run 13 | Run 14 | Run 15 |
|---|---|---|---|---|
| 1,3-Butadiene, p/w | 100 | 100 | 100 | 100 |
| Cyclohexane, p/w | 797 | 797 | 782 | 782 |
| 2-Methylpentadienyllithium mhm[a] | 20.1 | 20.1 | — | — |
| 3-Methylpentadienyllithium mhm[b] | — | — | 20.7 | 20.7 |
| Polymerization temp., °C. | 50 | 50 | 50 | 50 |
| Polymerization time, hours | 0.3 | 0.9 | 0.3 | 0.9 |

[a]Added as a 1.030 M sol. of approx. 2/1 by vol. THF/cyclohexane.
[b]Added as a 0.849 M sol. of approx. 2/1 by vol. THF/cyclohexane.

The conjugated unsaturation analysis of these polymers are shown in Table IV.

TABLE IV

Conjugated Unsaturation of 2-Methyl- and 3-Methylpentadienyllithium Initiated Polymers as a Function of Polymerization Time

| | | | Conjugated Unsaturation | |
|---|---|---|---|---|
| Run | Initiator | Polymerization Time, Hours | Found, Weight Percent | Percent of Theory |
| 12 | 2-MePdylLi[a] | 0.3 | 0.94 | 69 |
| 13 | 2-MePdylLi | 0.9 | 0.84 | 62 |
| 14 | 3-MePdLi[b] | 0.3 | 0.50 | 37 |
| 15 | 3-MePdLi | 0.9 | 0.03 | 2 |

[a]2-Methylpentadienyllithium
[b]3-Methylpentadienyllithium

These data demonstrate that living polymers having the terminal 2-methyl-2,4-pentadienyl functional group are less subject to self-polymerization than similar polymers having terminal 3-methyl-2,4-pentadienyl functional groups.

EXAMPLE V

Runs 16 and 17 demonstrate the self-polymerization of living medium vinyl polybutadiene. Medium vinyl polybutadiene was prepared using the general procedures described in Example I and according to Recipe V:

RECIPE V

| | Run 16 | Run 17 |
|---|---|---|
| 1,3-Butadiene, p/w | 100 | 100 |
| Cyclohexane, p/w | 796 | 820 |
| Pentadienyllithium, mhm[a] | 9.8 | 10.0 |
| Polym. temp., °C. | 50 | 50 |
| Polym. time, hours | 1.3 | 4.0 |

[a]Added as a 0.2644 M sol. vy vol. in approx. 10/1 benzene/THF.

Where no coupling agent is shown, termination was by alcohol.

TABLE V

Physical Properties of Polymers as a Function of Polymerization Time

| Run | Polym. Time, Hours | Monomer to Polymer Conv. Wt. % | I.V. | $M_w/M_n$ | H.I. | Conj. Wt. % Found | Conj. Wt. % Theory |
|---|---|---|---|---|---|---|---|
| 16 | 1.3 | 100 | 0.34 | 19,000 / 15,000 | 1.31 | 0.21 | 0.68 |
| 17 | 4.0 | 100 | 0.53 | 79,000 / 32,000 | 2.40 | 0.03 | 0.68 |

These data illustrate that self-polymerization of living polybutadiene having pentadienyl terminal groups occurs following quantitative conversion of monomer to polymer. The self-polymerization results in a loss of conjugated unsaturation, and a concurrent increase in inherent viscosity and molecular weight and a broadened molecular weight distribution (higher H.I.), as a function of time after quantitative conversion of monomer to polymer.

EXAMPLE VI

Runs 18 and 19 demonstrate the preparation of a multiple-branched polybutadiene by initiating the polymerization with pentadienyllithium; terminating the living polymer, after essentially quantitative conversion of monomer to polymer, with a stoichiometric amount of isopropyl alcohol; and then reinitiating the pentadienyl semi-telechelic polybutadiene with n-butyllithium.

Each polymer was prepared using the general procedures as described in Example I according to Recipe VI:

| RECIPE VI | |
|---|---|
| Step I | |
| 1,3-Butadiene, p/w | 100 |
| Cyclohexane, p/w | 792 |
| Pentadienyllithium, mhm[a] | 10.5 |
| Polym., temp. °C. | 50 |
| Polym., time, hours | 1.17 |
| Step II | |
| Isopropyl alcohol, mhm[b] | 10.6 |
| Reaction temp., °C. | 50 |
| Reaction time, hours | 0.67 |
| Step III | |
| n-Butyllithium, mhm[c] | 0.6 |
| Reaction temp., °C. | 50 |
| Reaction time, hours | 1.0 |
| STEP IV | |
| Reaction temp., °C. | 50 |
| Reaction time, hours | 16.5 |

[a]Added as a 0.1341 M sol. in approx. 20/1 by vol. benzene/THF.
[b]Added as a 1.50 M sol. in cyclohexane.
[c]Added as a 0.0611 M sol. in approx. 25/1 by vol. cyclohexane/n-heptane.

Samples of each polymer were recovered by coagulation with excess isopropyl alcohol and isolation by typical procedures after Steps II, III, and IV. Physical properties of these recovered polymers are given in Table VI:

TABLE VI

Physical Properties of Multiple Branched Polybutadienes

| Run | Polymerization Time, Hours Initial Polymerization[a] | After Reinitiation[b] | I.V. | $M_w/M_w$ | H.I. |
|---|---|---|---|---|---|
| 18 | 1.2 | 0 | 0.30 | 16,000 / 13,000 | 1.23 |
| 19 | 1.2 | 1.0 | 0.33 | 20,000 / 14,000 | 1.43 |
| 20 | 1.2 | 17.5 | 0.56 | 115,000 / 35,000 | 3.29 |

[a]Initiated with pentadienyllithium and terminated with isopropyl alcohol after essentially quantitative conversion of monomer to polymer.
[b]Isopropyl alcohol-terminated polymer reinitiated with n-butyllithium.

These data demonstrate that reinitiation of isopropyl alcohol-terminated polybutadiene, which has terminal conjugated dienyl groups, results in the formation of branched polymer having much higher molecular weight and much broader molecular weight distribution (heterogeneity index) than the originally terminated polymer, and that the molecular weight and the heterogeneity index increase as a function of time.

EXAMPLE VII

Runs 21 through 24 inclusive demonstrate the preparation of a highly branched, cross-linked polybutadiene by initiating the polymerization with pentadienyllithium, terminating with a difunctional coupling agent, and then reinitiating the pentadienyl telechelic polybutadiene with n-butyllithium.

Polymers were prepared, using the general procedures as described in Example I according to Recipe VII:

| RECIPE VII | |
|---|---|
| Step I | |
| 1,3-Butadiene, parts by weight | 100 |
| Cyclohexane, parts by weight | 810 |
| Pentadienyllithium, mhm[a] | 5.6 |
| Polym. temp., °C. | 50 |
| Polym. time, hours | 0.5 |
| Step II | |
| α,α'-Dichloro-p-xylene, mhm[b] | 2.8 |
| Reaction temp., °C. | 50 |
| Reaction time, hours | 0.75 |
| Step III | |
| n-Butyllithium, mhm[c] | 2.0 |
| Polym. temp., °C. | 50 |
| Polym. time, hours | 1.5 |
| Step IV | |
| Polym. temp., °C. | 50 |
| Polym. time, hours | 5.3 |

[a]Added as a 0.2613 M sol. in approx. 10/1 by vol. benzene/THF.
[b]Added as a 0.046 M sol. in cyclohexane.
[c]Added as a 0.1188 M sol. in approx. 12/1 by vol. cyclohexane/n-heptane.

Samples of each of the polymers were recovered after Steps I, II, III, and IV by coagulation with excess isopropyl alcohol and isolation by typical procedures. Physical properties of these recovered polymers are given in Table VII:

TABLE VII

Physical Properties of Highly Branched, Cross-Linked Polybutadiene

| Polymer Sample | Polymerization Time, Hours Polymerization | After Reinitiation | I.V. | $M_w/M_n$ | H.I. | Gel. Wt. % |
|---|---|---|---|---|---|---|
| 21[a] | 0.5 | 0 | 0.39 | 29,000 / 25,000 | 1.15 | 0 |

TABLE VII-continued

Physical Properties of Highly Branched, Cross-Linked Polybutadiene

| Polymer Sample | Polymerization Time, Hours Polymerization | Polymerization Time, Hours After Reinitiation | I.V. | $M_w/M_n$ | H.I. | Gel. Wt. % |
|---|---|---|---|---|---|---|
| 22[b] | 0.5 | 0 | 0.65 | 59,000 / 47,000 | 1.25 | 0 |
| 23[c] | 0.5 | 1.5 | 0.63 | 65,000 / 51,000 | 1.25 | 0 |
| 24[c] | 0.5 | 6.8 | 0.76 | — | — | 82 |

[a]Before coupling
[b]Coupled
[c]Coupled and reinitiated

These data illustrate that reinitiation of pentadienyl-telechelic polybutadiene with n-butyllithium results in the formation of a high molecular weight polymer which increases in molecular weight as a function of time and ultimately leads to a gelled product.

EXAMPLE VIII

Runs 25 through 28 inclusive demonstrate the polymerization of styrene with pentadienyllithium as initiator.

Polystyrene was prepared using the general procedures as described in Example I according to Recipe VIII:

RECIPE VIII

|  | Run 25 | Run 26 | Run 27 | Run 28 |
|---|---|---|---|---|
| Styrene, p/w | 100 | 100 | 100 | 100 |
| Cyclohexane, p/w | 668 | 663 | 668 | 663 |
| Tetrahydrofuran, p/w | 2.3 | 3.4 | 2.3 | 3.4 |
| n-Butyllithium, mhm[a] | 10.5 | 0 | 10.5 | 0 |
| Pentadienyllithium, mhm[b] | 0 | 10.5 | 0 | 10.5 |
| Polym. temp., °C. | 50 | 50 | 50 | 50 |
| Polym. time, hours | 1.3 | 1.4 | 17.9 | 18.1 |

[a]Added as a 0.1405 M sol. in approx. 10/1 by vol. cyclohexane/n-heptane.
[b]Added as a 0.443 M sol. in approx. 6/1 by vol. toluene/THF.

Per Example I, if no coupling agent is shown, then termination was with alcohol. Quantitative conversion of monomer to polymer occurred within 1.1 hours of polymerization initiation in all runs.

The physical properties of these polystyrene polymers are shown in Table VIII:

TABLE VIII

Physical Properties of Polystyrene Initiated with Pentadienyllithium

| Run | Initiator Type | Initiator mhm | Polymerization Time, hours | $M_w/M_n$ | H. I. |
|---|---|---|---|---|---|
| 25 | NBL[a] | 10.5 | 1.3 | 10,800 / 10,100 | 1.07 |
| 26 | PdylLi[b] | 10.5 | 1.4 | 77,000 / 52,000 | 1.48 |
| 27 | NBL | 10.5 | 17.9 | 13,600 / 12,500 | 1.09 |
| 28 | PdylLi | 10.5 | 18.1 | 121,000 / 53,000 | 2.28 |

[a]n-Butyllithium
[b]Pentadienyllithium

These data from Runs 25-28 inclusive demonstrate that at the same initiator concentration:

(A) the number average molecular weight ($M_n$) of polystyrene prepared using pentadienyllithium as initiator is 4 to 5 times greater than that obtained using n-butyllithium, and is also about 5 times the theoretical kinetic molecular weight. The kinetic molecular weight is defined as: weight of monomer polymerized/moles of initiator.

(B) the molecular weight distribution (heterogeneity index) of polystyrene prepared using pentadienyllithium is significantly broader than polystyrene prepared using n-butyllithium.

(C) maintaining the live polymer cement at the reaction temperature, after complete conversion of styrene monomer to polystyrene, results in a significant increase in molecular weight and broadening of the molecular weight distribution when pentadienyllithium is used as polymerization initiator, as compared to only very little increase when n-butyllithium is the initiator.

These results are consistent with a self-polymerization process, the reaction of polymerlithium with the terminal conjugated dienyl group of a second living polymerlithium and subsequent propagation reactions, after total conversion of monomer to polymer has occurred. It is believed that this self-polymerization process occurs not only after complete conversion of monomer, but is probably a competing reaction during polymerization of monomer to polymer.

EXAMPLE IX

Runs 29 and 30 demonstrate the preparation of butadiene-styrene copolymers by the sequential polymerization of first butadiene and then styrene, using pentadienyllithium as initiator.

The polymers were prepared according to the general procedures as described in Example I and Recipe IX:

RECIPE IX

| Step I. | Run 29 (Control) | Run 30 |
|---|---|---|
| 1,3-Butadiene, p/w | 82 | 80 |
| Benzene, p/w | 614 | 956 |
| Tetrahydrofuran, p/w | 0.71 | 0.6 |
| sec-Butyllithium, mhm[a] | 1.0 | — |
| Pentadienyllithium, mhm[b] | — | 1.6 |
| Polym. temp., °C. | 50 | 50 |
| Polym. time, hours | 2.2 | 1.3 |
| Step II |  |  |
| Styrene | 18 | 20 |
| Polym. temp., °C. | 50 | 50 |
| Polym. time, hours | 1.2 | 0.4 |

[a]Added as a 0.139 M solution in approx. 10/1 by vol. cyclohexane/n-heptane.
[b]Added as a 2.1 M sol. in approx. 2/5 by vol. benzene/THF.

Again, as in Example I, termination was with alcohol where no coupling agent is shown in the recipe.

Results are shown in Table IX:

TABLE IX

| Copolymer | Initiator | Green Tensile, MPa |
|---|---|---|
| Run 29 | sec-butyllithium | 0.5 |
| Run 30 | Pentadienyllithium | 10.1 |

The graft copolymer of Run 30 prepared using pentadienyllithium as initiator had a green tensile strength of 10.1 MPa compared to a value of only 0.5 MPa for the control block copolymer of Run 29 prepared using sec-butyllithium.

EXAMPLE X

Runs 31 and 32 inclusive demonstrate the preparation of butadiene-styrene graft copolymers prepared by the sequential polymerization of butadiene and styrene using pentadienyllithium as initiator, and their evaluation in an adhesive formulation.

Polymers were prepared according to the general procedures described in Example I and Recipe X:

RECIPE X

| Step I | Run 31 | Run 32 |
|---|---|---|
| 1,3-Butadiene, p/w | 70 | 71 |
| Benzene, p/w | 855 | 881 |
| Pentadienyllithium, mhm[a] | 1.8[a] | 2.9[b] |
| Polym. temp., °C | 50 | 50 |
| Polym. time, hours | 1.3 | 1.1 |
| Step II | | |
| Styrene, p/w | 30 | 29 |
| Polym. temp., °C | 50 | 50 |
| Polym. time, hours | 0.3 | 0.6 |

[a] Added as a 2.1 M sol. in approx. 2/5 by vol. benzene/THF.
[b] Added as a 0.137 M sol. in approx. 21/1 by vol. benzene/THF.

Termination was with alcohol where no coupling agent is shown.

Physical properties of the two polymers of Runs 31–32 as compared to a commercial 70/30 butadiene/styrene radial teleblock copolymer prepared by initiation with n-butyllithium are shown in Table X-A:

TABLE X-A

Physical Properties of Butadiene-Styrene Graft Copolymers

| | Radial Teleblock Control | Graft-Block Copolymers | |
|---|---|---|---|
| | | Run 31 | Run 32 |
| I.V. | 1.45 | 1.58 | 1.48 |
| $M_w$ | 300,000 | 356,000 | 332,000 |
| $M_n$ | 220,000 | 143,000 | 119,000 |
| H.I. | 1.4 | 2.5 | 2.8 |

These three polymers, the inventive graft polymers 31 and 32, and the comparison (control), were evaluated as adhesives in the following formulation:

Adhesive Formulation

| Ingredient | Parts by Weight |
|---|---|
| Rubbery Polymer | 15.00 |
| Foral 85[a] | 15.00 |
| Irganox 1076[b] | 0.15 |
| Toluene | 69.85 |

[a] A highly stabilized rosin ester tackifier from Hercules, Inc.
[b] An antioxidant having the structure n-octadecyl [3-(3,5-di-t-butyl-4-hydroxyphenyl)]propionate from Ciba-Geigy Corp.

Adhesive properties of the formulations based on the control and two inventive graft copolymers of Runs 31 and 32 are shown in Table X-B:

TABLE X-B

Adhesive Properties of formulations Based on Graft Copolymers

| Property | Radial Teleblock Control | Graft-Block Copolymer | |
|---|---|---|---|
| | | Run 31 | Run 32 |
| Holding power, hours to 1.6 mm[a] | | | |
| 60° C., 0.454 kg (1 pound) | >24 | >24 | >24 |
| 85° C., 0.907 kg (2 pounds) | 14.3 | 4.9 | 0.3 |
| Polyken probe tack, grams[b] | | | |
| Initial | 790 | 790 | 825 |
| After 7 days at 25° C. | 670 | 640 | 670 |
| After 7 days at 70° C. | 600 | 520 | 650 |
| Rolling Ball Tack, cm[c] | | | |
| Initial | 3.3 | 4.8 | 15.2 |
| After 7 days at 25° C. | 5.6 | 4.8 | 7.9 |
| After 7 days at 70° C. | 4.8 | 5.3 | 6.6 |

[a] Measured as time in hours for 1.6 mm slippage when 1 inch$^2$ of adhesive on Mylar film backing is bonded to stainless steel and loaded in shear; higher number represents better creep resistance.
[b] Measured using Polyken Probe tack tester manufactured by Testing Machine Inc. Test conditions were: probe speed, 1 cm/sec.; dwell time, 1 sec.; contact force, 100 g/cm.$^2$; higher number represents a higher degree of tack.
[c] Measured in centimeters as described in Pressure Sensitive Tape Council publication PSTC-6 (10/64); higher number represents a lower degree of tack.

These data illustrate the suitability of the graft-block butadiene/styrene copolymers for use in adhesives.

EXAMPLE XI

Runs 33–39 inclusive demonstrate the preparation of butadiene-styrene graft copolymers using the sequential addition procedure with pentadienyllithium as initiator as described in Example X, with the modification that the polybutadiene formed in the first step was allowed to self-polymerize (self-couple) for varying lengths of time prior to addition of the styrene monomer.

Polymers were prepared according to the general procedures described in previous examples and Recipe XI:

RECIPE XI

| Step I | |
|---|---|
| 1,3-Butadiene, p/w | 70 |
| Cyclohexane, p/w | 804 |
| Pentadienyllithium, mhm[a] | 3.5 |
| Polym. temp., °C | 50 |
| Polym. time, hours | variable |
| Step II | |
| Styrene, p/w | 30 |
| Polym. temp., °C | 50 |
| Polym. time, hours | variable |

[a] Added as a 0.2613 M sol. in approx. 10/1 benzene/THF.

Properties of the butadiene-styrene graft block copolymers of Runs 33–39 produced at varying polymerization times are shown in Table XI:

TABLE XI

| Run | Butadiene Polymerization Hours | Styrene Polymerization Hours | Polybutadiene Block | | | |
|---|---|---|---|---|---|---|
| | | | I. V. | $M_w/M_n$ | H. I. | Gel, Wt. % |
| 33 | 0.5 | 0.5 | 0.39 | 26,000 / 23,000 | 1.13 | 0 |
| 34 | 0.75 | 0.5 | 0.42 | 29,000 / 25,000 | 1.14 | 0 |
| 35 | 1.0 | 0.5 | 0.44 | 34,000 / 29,000 | 1.16 | 0 |
| 36 | 1.5 | 0.5 | 0.48 | 36,000 / 30,000 | 1.20 | 0 |
| 37 | 2.0 | 0.5 | 0.50 | 43,000 / 34,000 | 1.25 | 0 |
| 38 | 3.2 | 0.6 | 0.55 | 53,000 / 39,000 | 1.35 | 0 |
| 39 | 9.4 | 0.75 | 1.45 | — | — | 14 |

Butadiene-Styrene Graft Copolymer

| Run | I. V. | $M_w/M_n$ | H. I. | Gel, Wt. % | Green Tensile Strength, MPa |
|---|---|---|---|---|---|
| 33 | 1.34 | 357,000 / 125,000 | 2.9 | 0 | 3.0 |
| 34 | 1.31 | 319,000 / 114,000 | 2.8 | 0 | 10.1 |

TABLE XI-continued

| | | | | | |
|---|---|---|---|---|---|
| 35 | 1.32 | 289,000/109,000 | 2.7 | 0 | 14.9 |
| 36 | 1.23 | 303,000/116,000 | 2.6 | 0 | 16.6 |
| 37 | 1.22 | 331,000/119,000 | 2.8 | 0 | 16.0 |
| 38 | 1.35 | 391,000/134,000 | 2.9 | 0 | 17.4 |
| 39 | 1.74 | 826,000/168,000 | 4.9 | 0 | 8.5 |

These data illustrate the self-polymerization (self-coupling) of the polybutadiene block as a function of time, and also the significantly greater rate of self-polymerization (self-coupling) of the polystyryllithium terminated polymer as shown by the 200 to 500% increase in molecular weight upon adding styrene to the live polybutadiene polymer. As comparison, sequential polymerization of a 70/30 ratio of butadiene/styrene using approximately 3.5 mhm of a saturated organo monolithium, such as n-butyllithium, normally results in less than a 50% increase in molecular weight upon adding the styrene to the live polybutadiene polymer. The self-polymerization or self-coupling which occurs according to one aspect of the invention is shown to result in a significant increase in green tensile strength.

EXAMPLE XII

Runs 40–43 inclusive demonstrate the preparation of high styrene-containing butadiene/styrene copolymers and their evaluation as impact resistant resins.

Polymers were prepared according to the general procedures described previously and Recipe XII:

| RECIPE XII | | | | |
|---|---|---|---|---|
| Step I | Run 40 | Run 41 | Run 42 | Run 43 |
| 1,3-Butadiene, p/w | 10 | 10 | 20 | 20 |
| Styrene, p/w | 90 | 90 | 80 | 80 |
| Benzene, p/w | 804 | 777 | 800 | 806 |
| n-Butyllithium, mhm$^{(a)}$ | 0.87 | — | 1.1 | — |
| Pentadienyllithium, mhm$^{(b)}$ | — | 1.45 | — | 2.4 |
| Polym. temp., °C. | 50 | 50 | 50 | 50 |
| Polym. time, hours | 2.1 | 1.4 | 1.25 | 1.25 |

$^{(a)}$Added as a 0.135 M sol. in approx. 10/1 by vol. benzene/n-heptane.
$^{(b)}$Added as a 0.124 M sol. in approx. 23/1 by vol. benzene/THF.

Physical properties of these high styrene-containing resins of Runs 40–43 inclusive are shown in Table XII:

TABLE XII

Physical Properties of High Styrene-Containing Butadiene/Styrene Copolymers

| | Run 40 Control | Run 41 | Run 42 Control | Run 43 |
|---|---|---|---|---|
| Butadiene/styrene, wt. ratio | 10/90 | 10/90 | 20/80 | 20/80 |
| Initiator | NBL$^{(a)}$ | PdylLi$^{(b)}$ | NBL$^{(a)}$ | PdylLi$^{(b)}$ |
| Block polystyrene$^{(c)}$, wt. % | 76 | 65 | 63 | 47 |
| M$_w$ | 180,000 | 501,000 | 132,000 | 329,000 |
| M$_n$ | 160,000 | 228,000 | 115,000 | 145,000 |
| H. I. | 1.1 | 2.2 | 1.1 | 2.3 |
| I. V. | 0.88 | 1.01 | 0.76 | 0.81 |
| Melt Index, 200° c./5 Kg$^{(d)}$ | 1.4 | 1.9 | 4.3 | 7.8 |
| Flexural modulus, MPa$\times 10^{-3(e)}$ | 2.1 | 2.0 | 1.5 | 0.6 |
| Tensile, MPa | 40.9 | 39.1 | 27.0 | 12.3 |
| Elongation, % | 4 | 10 | 5 | 186 |
| Hardness, Shore D$^{(f)}$ | 80 | 83 | 73 | 73 |
| Dart impact, kg · m$^{(g)}$ | <0.115 | 0.115 | 0.196 | >0.92 |

$^{(a)}$n-Butyllithium.
$^{(b)}$Pentadienyllithium.
$^{(c)}$Based on technique described by I. M. Kolthoff, T. S. Lee, and C. W. Carr, J. Poly. Sci. 1, 429 (1946).
$^{(d)}$ASTM D1238-73, condition G.
$^{(e)}$ASTM D790-71.
$^{(f)}$ASTM D2240-75.
$^{(g)}$A 0.509 kg (1.123 pounds) dart is dropped onto horizontally-mounted injection molded test specimens measuring approximately 8.38 cm. by 3.56 cm. by 0.254 cm. (3.3 inches by 1.4 inches by 0.1 inch) from various heights measured at 5.08 cm (2 inch) intervals above the test specimen. By a trial and error procedure the maximum height is determined at which a set of 4 test specimens are not broken. The dart is then dropped on 4 additional test specimens from a 5.08 cm (2 inch) higher height and the percentage of specimens which break are recorded. This procedure is repeated at consecutive 5.08 cm higher intervals until a height is attained at which all 4 test specimens of a given set break. The "dart impact" is determined by first calculating a value designated as F$_{50}$ from the equation $$F_{50} = I_H + \Delta I \left( \frac{S}{100} - 0.5 \right)$$

wherein F$_{50}$ = Height in meters for failure of 50% of test specimens
I$_H$ = Lowest height in meters at which all 4 test specimens of a given set fail
I = Height increments in meters
S = Sum of the "percentage of failures" for each set of 4 test specimens tested at the various heights, including the height wherein no breaks occurred, and all inclusive of each incremental height up to and including I$_H$.
The dart impact then is calculated from:
Dart Impact = F$_{50}$ × weight of dart = kg · m.

The significantly higher molecular weight and broader molecular weight distribution of the pentadienyllithium-initiated polymers of Runs 41 and 43 indicate the occurrence of self-polymerization of self-coupling during polymerization, which resulted in 10/90 and 20/80 butadiene-styrene resins having improved elongation and dart impact strength as compared to the n-butyllithium-initiated control polymers of Runs 40 and 42.

EXAMPLE XIII

These runs illustrate the preparation of linear medium vinyl polybutadienes having small terminal blocks of low vinyl polybutadiene or 1,4-polymerized isoprene, using hexadienyllithium as initiator, and the evaluation of the vulcanizate properties of these polymers.

Hexadienyllithium was prepared as described in Example III. The polymers were prepared according to the general procedure described in Example I and Recipe XIII:

| RECIPE XIII | | | | |
|---|---|---|---|---|
| Step I | Run 44 (control) | Run 45 | Run 46 (control) | Run 47 |
| 1,3-Butadiene, parts by weight | — | — | 30 | 30 |
| Isoprene, parts by weight | 30 | 30 | — | — |
| Cyclohexane, parts by weight | 800 | 800 | 800 | 800 |
| Tetrahydrofuran, parts by weight | 3.6 | — | — | — |
| n-Butyllithium, mhm$^{(a)}$ | 1.4 | — | 1.2 | — |
| Hexadienyllithium, mhm$^{(b)}$ | — | 1.5 | — | 1.7 |
| Polymerization temperature, °C. | 70 | 70 | 70 | 70 |

-continued

| | RECIPE XIII | | | |
|---|---|---|---|---|
| Step I | Run 44 (control) | Run 45 | Run 46 (control) | Run 47 |
| Polymerization time, hours | 1.0 | 1.0 | 1.0 | 0.75 |
| Step II | | | | |
| 1,3-Butadiene, parts by weight | 70 | 70 | 70 | 70 |
| Tetrahydrofuran, parts by weight | — | 3.2 | 3.6 | 3.2 |
| Polymerization temperature, °C. | 70 | 50 | 50 | 50 |
| Polymerization time, hours | 0.5 | 0.75 | 1.0 | 0.75 |
| Step III | | | | |
| α,α'-dichloro-p-xylene, mhm[c] | 0.66 | 0.74 | 0.62 | 0.84 |
| Reaction temperature, °C. | 70 | 70 | 70 | 70 |
| Reaction time, hours | 0.25 | 0.5 | 0.25 | 0.25 |

[a] Added as a 0.153M solution in approximately 14/1 by volume cyclohexane/n-heptane.
[b] Added as a 0.194M solution in approximately 21/1 by volume toluene/THF.
[c] Added as a 0.0895M or a 0.0909M solution in cyclohexane.

These polymers were compounded according to the general procedure and formulation of Recipe II given in Example II. Properties of the vulcanized compounded rubbers are shown in Table XIII:

TABLE XIII

Properties of Compounded and Vulcanized[a] Hexadienyl Terminated Conjugated Diene Triblock Polymers

| | Polymer Prepared In | | | |
|---|---|---|---|---|
| Property | Run 44 (control) | Run 45 | Run 46 (control) | Run 47 |
| Raw Mooney viscosity, ML-4 at 100° C. | 39 | 38 | 43 | 37 |
| Compounded Mooney viscosity, ML-4 at 100° C. | 58 | 58 | 74 | 56 |
| Tensile (23° C.), MPa | 17.3 | 18.1 | 16.2 | 16.2 |
| Elongation (23° C.), percent | 420 | 410 | 395 | 400 |
| 200% Modulus (23°C.), MPa | 5.4 | 5.8 | 5.5 | 5.4 |
| 300% Modulus (23° C.), MPa | 10.3 | 11.3 | 10.5 | 10.5 |
| Compression set, percent | 14.1 | 13.5 | 13.4 | 15.5 |
| ΔT, ° C. | 29.0 | 25.1 | 30.8 | 31.3 |
| Resilience, percent | 65.2 | 70.9 | 69.1 | 69.6 |
| Hardness, Shore A | 60 | 59 | 63 | 61 |

[a] Vulcanized for 45 minutes at 150° C.

These data demonstrate the superior vulcanizate properties of the isoprene-butadiene teleblock polymer having the terminal hexadienyl groups (Run 45) compared to the control isoprene butadiene teleblock copolymer without the hexadienyl terminal groups (Run 44). Especially noteworthy is the significantly better heat build-up (ΔT) and resilience properties. However, it should be noted that the polymers may have somewhat different microstructure in the polyisoprene blocks due to the presence of tetrahydrofuran during the polymerization of the isoprene in the control Run 44, while in the invention Run 45 no tetrahydrofuran was present during isoprene polymerization. This difference in fine structure may account at least in part for the difference in properties of the compounded rubbers.

Data for the low vinyl-medium vinyl butadiene teleblock polymers did not show an improvement in properties as a function of the presence of a hexadienyl terminal groups (compare Runs 46 and 47). This may have been due to the lower Mooney viscosity of the hexadienyl terminated polymer (Run 47). If the polymers of Runs 46 and 47 had had the same Mooney viscosity, it is believed that the heat build-up and the resiliency of the hexadienyl terminated polymer of Run 47 would have been superior to the control polymer 46.

EXAMPLE XIV

These runs illustrate the preparation of a linear telechelic pentablock polymer having terminal hexadienyl groups and the evaluation of the vulcanizate properties of this polymer.

Hexadienyllithium was prepared as described in Example III. The polymer was prepared according to the general procedure described in Example I and Recipe XIV-A:

| RECIPE XIV-A | |
|---|---|
| | Run 48 |
| Step I | |
| Isoprene, parts by weight | 20 |
| Cyclohexane, parts by weight | 800 |
| Tetrahydrofuran, parts by weight | 3.6 |
| Hexadienyllithium, mhm[a] | 2.2 |
| Polymerization temperature, ° C. | 50, 70 |
| Polymerization time, hours | 0.13, 0.75 |
| Step II | |
| Styrene, parts by weight | 15 |
| Polymerization temperature, °C. | 70 |
| Polymerization time, hours | 0.75 |
| Step III | |
| 1,3-Butadiene, parts by weight | 65 |
| Polymerization temperature, °C. | 70 |
| Polymerization time, hours | 0.75 |
| Step IV | |
| α,α'-Dichloro-p-xylene, mhm[b] | 1.1 |
| Reaction temperature, °C. | 70 |
| Reaction time, hours | 0.2 |

[a] Added as a 0.128M solution is approximately 12/1 by volume cyclohexane/n-heptane.
[b] Added as a 0.088M solution in cyclohexane.

This polymer was compounded according to the general procedure given in Example III and Recipe XIV-B:

| RECIPE XIV-B | |
|---|---|
| Ingredient | Parts by Weight |
| Rubber | 100 |
| Carbon black[a] | 55 |
| Naphthenic oil[b] | 6 |
| Zinc oxide | 5 |
| Stearic acid | 2 |
| AgeRite Resin D[c] | 1.5 |
| AgeRite White[d] | 0.5 |
| Crystex insoluble sulfur[e] | 2.5 |
| Santocure NS[f] | 0.9 |

[a] Philblack ® N-339; Phillips Petroleum Co.
[b] Circosol 4240; Sun Oil Company; described by ASTM D2226, Type 103; contains 47.5% aromatics.
[c] An antioxidant; polymerized 1,2-dihydro-2,2,4-trimethylquinoline; R. T. Vanderbilt.
[d] An antioxidant; symmetrical di-β-naphthyl-p-phenylenediamine; R. T. Vanderbilt.
[e] Oil-treated Crystex, 20% polymerized sulfur; Stauffer Chemical.
[f] An accelerator; N-t-butyl-2-benzothiazolesulfenamide; Monsanto.

Properties of the vulcanized compound rubber are shown in Table XIV:

TABLE XIV

| Properties of Compounded and Vulcanized[a] Hexadienyl Terminated Isoprene-Styrene-Butadiene-Styrene-Isoprene Pentablock Copolymer | |
|---|---|
| Property | Run 48 |
| Raw Mooney viscosity, ML-4 at 100° C. | 111 |
| Compounded Mooney viscosity, MS-4 at 100° C. | 63 |
| Tensile (23° C.), MPa | 21.6 |
| Elongation (23° C.), percent | 380 |
| 200% Modulus (23° C.), MPa | 10.9 |
| 300% Modulus (23° C.), MPa | 17.4 |
| Compression set, percent | 22.1 |
| ΔT, °C. | 35.5 |
| Resilience, percent | 65.0 |
| Hardness, Shore A | 75 |

[a] Vulcanized for 30 minutes at 150° C.

These data illustrate that a pentablock copolymer having terminal hexadienyl groups has good vulcanizate properties.

The disclosure, including data, illustrate the value and effectiveness of our invention. The examples, the knowledge and background of the field of the invention and of general principles of chemistry and other applicable sciences, have formed the bases from which the broad descriptions of the invention including the ranges of conditions and the generic groups of operant components have been developed, and have formed the bases for our claims here appended.

We claim:

1. A process which comprises the steps of
(A) polymerizing to substantially complete conversion at least one first polymerizable olefinically unsaturated monomer under anionic solution polymerization conditions employing a dienyllithium initiator, thereby resulting in a polymerization admixture containing polymer terminated at least in part with a conjugated dienyl functional group,
wherein said dienyllithium initiator is a product prepared by contacting at least one hydrocarbon lithium compound $R(Li)_x$ with at least one hydrocarbon 1,4-diolefin in a mixed solvent of saturated hydrocarbon/polar compound, under dienyllithium initiator forming temperature conditions, wherein R is a hydrocarbyl radical of valence x, and x is an integer of 1 to 4;
(B) treating said polymerization admixture containing polymer terminated at least in part with a conjugated dienyl functional group by a treating mode to produce a polymer selected from the group consisting of:
(a) a polymer produced by treating with an effective amount of at least one polyfunctional coupling agent of at least difunctionality, thereby preparing at least in part a coupled conjugated dienyl terminated polymer if increased molecular weight characterized by conjugated dienyl groups on the extending terminal ends of the coupled polymer;
(b) a polymer produced by treating with at least one unsaturated compound selected from the group consisting of alicyclic conjugated trienes and tetraenes, and linear conjugated dienes, thereby providing a polymer containing at least in part terminal conjugated unsaturation at both ends of the polymer chain;
(c) a polymer produced by treating with an active hydrogen-containing compound sufficient to terminate active lithium, and thereafter reinitiating polymerization with a hydrocarbon lithium initiator $R(Li)_x$, with or without the further addition of a second polymerizable monomer the same or different from said first polymerizable monomer, thereby forming a branched polymer with broadened molecular weight;
(d) a polymer produced by maintaining said conjugated dienyl terminated polymer at substantially polymerization temperatures for a time sufficient to effect at least partial self-coupling, and thereafter adding a second polymerization monomer and polymerizing thereonto, thereby resulting in a branched polymer at least in part;
(e) a polymer produced by treating as defined by substep (a) above followed by reinitiating polymerization with a further addition of a hydrocarbon lithium initiator $R(Li)_x$, with or without the further addition of a second polymerizable monomer the same or different from said first polymerizable monomer, thereby resulting at least in part in a branched polymer;
(C) wherein when any polymer resulting from any of said (a) through (e) inclusive retains active lithium, thereafter treating with an active hydrogen-containing compound effective to terminate said active lithium.

2. The process according to claim 1 wherein said $R(Li)_x$ in said step (A), and in said (c) and (e) where employed, said R hydrocarbon radical contains 1 to 20 carbon atoms per molecule, and wherein in said step (A) said hydrocarbon 1,4-diolefin contains 5 to 12 carbon atoms per molecule.

3. The process according to claim 2 wherein said hydrocarbon 1,4-diolefin is selected from the group consisting of 1,4-pentadiene, 2-methyl-1,4-pentadiene, 3-methyl-1,4-pentadiene, 1,4-hexadiene, 1-methyl-1,4-cyclohexadiene, terpinolene, β-terpinene, and α-terpinene.

4. The process according to claim 3 wherein said $R(Li)_x$ is selected from the group consisting of methyllithium, isopropyllithium, n-butyllithium, sec-butyllithium, tert-butyllithium, n-decyllithium, phenyllithium, naphthyllithium, 4-butylphenyllithium, p-tolyllithium, 4-phenylbutyllithium, cyclohexyllithium, 1,4-dilithiobutane, 1,20-dilithioeicosane, 1,4-dilithiocyclohexane, 1,5-dilithionaphthalene, 1,3,5-trilithiopentane, and 1,2,4,6-tetralithiocyclohexane.

5. The process according to claim 4 wherein in said step (A) said at least one polymerizable monomer is selected from the group consisting of conjugated dienes, monovinylarenes, acrylic and alkacrylic acid esters, vinyl pyridines, vinylidene halides, vinylquinolines, nitriles, N,N-disubstituted acrylamides, vinylfuran, N-vinyl carbazole, and mixtures.

6. The process according to claim 5 wherein said step (A) contacting employs a ratio of $R(Li)_x$: hydrocarbon 1,4-diolefin of about 0.9:1 to 1.1:1, a mixed solvent volume ratio of about 20:1 to 2:1 saturated hydrocarbon:-polar component, and a temperature in the range of about $-100°$ C. to 30° C.

7. The process according to claim 6 wherein said treating mode (B) is with said (c) wherein said active hydrogen-containing compound is selected from the group consisting of lower alcohols.

8. The process according to claim 6 wherein said treating mode (B) is with said (a) wherein said functional treating agent is selected from the group consisting of multivinyl aromatic compounds, multiepoxides, multiisocyanates, multiimides, multialdehydes, multiketones, multihalides, multianhydrides, multiesters, combination-type agents, carbon oxides, sulfur halides, and the halogens.

9. The process according to claim 6 wherein said treating mode (B) is with said (b) with said alicyclic conjugated diene or tetraene or linear conjugated diene.

10. The process according to claim 9 wherein in said (b) said alicyclic conjugated diene or tetraene or linear conjugated diene has the structure selected from the group consisting of:

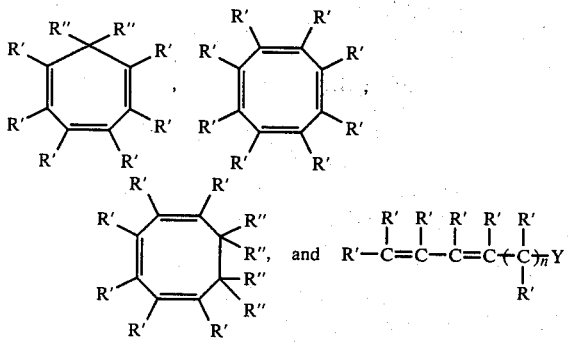

wherein each R' is hydrogen or alkyl such that the total number of carbon atoms in the molecule does not exceed 20 carbon atoms; R" is selected from the group consisting of R' and halogen such that only one R" per molecule can be halogen; n is an integer of 1 to 6; and Y is a functional group readily reactable with lithium on the polymer.

11. The process according to claim 10 employing said alicyclic conjugated triene or tetraene and selected from the group consisting of 1,3,5-cycloheptatriene, cyclooctatetraene, 5-chloro-1,3-pentadiene, 7-chloro-1,3,5-cycloheptatriene, 7-bromo-1,3,5-cyclooctatriene, and 7-chloro-1-methyl-1,3,5-cycloheptatriene.

12. The process according to claim 8 wherein in said step (A) said first polymerizable monomer is 1,3-butadiene and said dienyllithium initiator is pentadienyllithium, and wherein in said treating mode (B) (a) said polyfunctional treating agent is α,α-dichloro-p-xylene.

13. The process according to claim 11 wherein in said step (A) said first polymerizable monomer is 1,3-butadiene and said dienyllithium initiator is pentadienyllithium, and wherein in said treating mode (B) (b) said unsaturated compound is 5-chloro-1,3-petntadiene.

14. The process according to claim 8 wherein in said (A) said first polymerizable monomer is 1,3-butadiene and said dienyllithium initiator is 2-methylpentadienyllithium, and wherein in said treating mode (B) (a) said polyfunctional treating agent is α,α'-dichloro-p-xylene.

15. The process according to claim 8 wherein in said step (A) said first polymerizable monomer is 1,3-butadiene and said dienyllithium initiator is 3-methylpentadienyllithium, and wherein in said treating mode (B) (a) said polyfunctional treating agent is a multihalide and is α,α'-dichloro-p-xylene.

16. The process according to claim 8 wherein in said step (A) said first polymerizable monomer is 1,3-butadiene and said dienyllithium initiator is terpinyllithium, and wherein in said treating mode (B) (a) said polyfunctional treating agent is a multihalide and is α,α'-dichloro-p-xylene.

17. The process according to claim 8 wherein in said step (A) said first polymerizable monomer is 1,3-butadiene and said dienyllithium initiator is hexadienyllithium, and wherein in said treating mode (B) (a) said polyfunctional treating agent is a multihalide and is α,α'-dichloro-p-xylene.

18. The process according to claim 8 wherein in said step (A) said first polymerizable monomer is 1,3-butadiene and said dienyllithium initiator is pentadienyllithium, and wherein said treating mode (B) is with said (e).

19. The process according to claim 7 wherein in said step (A) said first polymerizable monomer is 1,3-butadiene and said dienyllithium initiator is pentadienyllithium, and wherein said treating mode (B) (c) is without a said second polymerizable monomer.

20. The process according to claim 6 wherein in said step (A) said first polymerizable monomer is 1,3-butadiene and said dienyllithium initiator is pentadienyllithium, and wherein said treating mode (B) employs said (e) wherein said polyfunctional treating agent is a multihalide and is α,α'-dichloro-p-xylene and said $R(Li)_x$ in said substep (e) is n-butyllithium.

21. The process according to claim 6 wherein in said step (A) said first polymerizable monomer is styrene and said dienyllithium initiator is pentadienyllithium, and said treating mode (B) is with said (e).

22. The process according to claim 6 wherein in said step (A) said first polymerizable monomer is 1,3-butadiene followed by styrene and said dienyllithium initiator is pentadienyllithium, and wherein said treating mode (B) is with said (e).

23. The process according to claim 8 wherein in said step (A) said first polymerizable monomer is isoprene followed by butadiene and said dienyllithium initiator is pentadienyllithium, and wherein said treating mode (B) is with said (a).

24. The process according to claim 8 wherein in said step (A) said first polymerizable monomer is isoprene followed by styrene followed by butadiene and said dienyllithium initiator is pentadienyllithium, and wherein said treating mode (B) is with said (a).

25. A polymer produced by the steps which comprise (A) polymerization of at least one olefinically unsaturated monomer selected from the group consisting of conjugated dienes, monovinylarenes, acrylates, vinylpyridines, vinylidene halides, and vinylquinolines, under anionic solution polymerization conditions employing a dienyllithium initiator, thereby resulting in a polymer terminated at least in part with a conjugated dienyl functional group, wherein said dienyllithium initiator is a reaction product of at least one hydrocarbon lithium compound $R(Li)_x$ with at least one hydrocarbon 1,4-diolefin in a mixed solvent of saturated hydrocarbon/polar compound, under dienyllithium initiator forming temperature conditions, wherein R has a valence of x and is a hydrocarbyl radical of 1 to 20 carbons wherein x is an integer of 1 to 4, and (B) thereafter treating said polymer containing at least in part conjugated dienyl functional group termination by a treating mode to produce a polymer selected from the group consisting of:

(a) a polymer produced by treating with an effective coupling amount of a polyfunctional coupling agent of at least difunctionality, thereby at least in part coupling said conjugated dienyl terminated polymer and resulting in a coupled polymer of increased molecular weight and characterized by conjugated dienyl groups on the extending ends of the coupled polymer, (b) a polymer produced by treating with an unsaturated compound selected from the group consisting of alicyclic conjugated trienes and tetraenes, and linear conjugated dienes, in an amount effective to provide about one mole of said unsaturated compound per equivalent of lithium initiator employed in said (A), thereby providing a polymer containing at least in part terminal conjugated unsaturation at each end of the polymer chain, (c) a polymer produced by treating with an active hydrogen-containing compound sufficient to terminate active lithium, and thereafter reinitiating polymerization with an organolithium initiator $R(Li)_x$, with or without the further addition of a second polymerizable monomer the same or different from said first polymerizable monomer, thereby forming a branched polymer with broadened molecular weight, (d) a polymer produced by maintaining said conjugated dienyl terminated polymer at polymerization temperatures for a time sufficient to effect at least partial self-coupling, and thereafter adding a second polymerizable monomer and polymerizing thereonto to produce a branched polymer, and (e) a polymer produced by treating as per (a) above followed by reinitiating polymerization with an organolithium initiator $R(Li)_x$, with or without the further addition of a second polymerizable monomer the same or different from said first polymerizable monomer; and thereafter (C) terminating any remaining active lithium.

26. The polymer according to claim 25 wherein in said step (A) said first polymerizable monomer is 1,3-butadiene and said dienyllithium initiator is pentadienyllithium, and wherein said treating step (B) is with said mode (b) wherein said unsaturated compound is 5-chloro-1,3-pentadiene.

27. The polymer according to claim 25 wherein in said step (A) said first polymerizable monomer is 1,3-butadiene and said dienyllithium initiator is 2-methyl-pentadienyllithium, and wherein said treating step (B) is said mode (a) employing a multihalide which is $\alpha,\alpha'$-dichloro-p-xylene.

28. The polymer according to claim 25 wherein in said step (A) said first polymerizable monomer is 1,3-butadiene and said dienyllithium initiator is 3-methyl-pentadienyllithium, and wherein said treating step (B) is said mode (a) employing a multihalide which is $\alpha,\alpha'$-dichloro-p-xylene.

29. The polymer according to claim 25 wherein in said step (A) said first polymerization monomer is 1,3-butadiene and said dienyllithium initiator is terpinyllithium, and wherein said treating step (B) is said mode (a) employing a multihalide which is $\alpha,\alpha'$-dichloro-p-xylene.

30. The polymer according to claim 25 wherein in said step (A) said first polymerizable monomer is 1,3-butadiene and said dienyllithium initiator is hexadienyllithium, and wherein said treating step (B) is said mode (a) employing a multihalide which is $\alpha,\alpha'$-dichloro-p-xylene.

31. The polymer according to claim 25 wherein in said step (A) said first polymerizable monomer is 1,3-butadiene and said dienyllithium initiator is pentadienyllithium, and wherein said treating step (B) is said mode (e).

32. The polymer according to claim 25 wherein in said step (A) said first polymerizable monomer is 1,3-butadiene and said dienyllithium initiator is pentadienyllithium, and wherein said treating step (B) is said mode (c) without a said second polymerizable monomer.

33. The polymer according to claim 25 wherein in said step (A) said first polymerizable monomer is 1,3-butadiene and said dienyllithium initiator is pentadienyllithium, and wherein said treating step (B) is said mode (e) including the further addition of a second polymerizable monomer wherein said coupling agent is a multihalide and is $\alpha,\alpha'$-dichloro-p-xylene and said $R(Li)_x$ in said step (e) is n-butyllithium.

34. The polymer according to claim 25 wherein in said step (A) said first polymerizable monomer is styrene and said dienyllithium initiator is pentadienyllithium, and wherein said treating step (B) is said (e).

35. The polymer according to claim 25 wherein in said step (A) said first polymerizable monomer is 1,3-butadiene followed by styrene and said dienyllithium initiator is pentadienyllithium, and wherein said treating step (B) is said mode (c).

36. The polymer according to claim 25 wherein in said step (A) said first polymerizable monomer is isoprene followed by butadiene and said dienyllithium initiator is pentadienyllithium, and wherein said treating step (B) is said mode (a).

37. The polymer according to claim 25 wherein said polymerization step (A) employs a sequential polymerization of isoprene followed by styrene followed by butadiene as said first polymerizable monomer and said dienyllithium initiator is pentadienyllithium, and wherein said treating step (B) is said mode (a).

38. The polymer according to claim 25 wherein said treating step (B) employs said mode (a).

39. The polymer according to claim 25 wherein said treating step (B) employs said mode (b).

40. The polymer according to claim 25 wherein said treating step (B) employs said mode (c) without further monomer addition.

41. The polymer according to claim 25 wherein said treating step (B) employs said mode (c) with said further monomer addition.

42. The polymer according to claim 25 wherein said treating step (B) employs said mode (d).

43. The polymer according to claim 25 wherein said treating step (B) employs said mode (e) without further monomer addition.

44. The polymer according to the process of claim 25 wherein said treating step (B) employs said mode (e) with said further monomer addition.

45. A process of preparing a hexadienyl terminated isoprene-styrene-butadiene-styrene-isoprene pentablock copolymer prepared according to the process of claim 1 wherein in said step (a) said polymerizing of at least one first polymerizable monomer employs the sequential addition and polymerization firstly of isoprene, followed by styrene, followed by 1,3-butadiene, employing hexadienyllithium as said dienyllithium initiator, and wherein said step (B) employs said substep (a) wherein said polyfunctional treating agent is $\alpha,\alpha'$-dichloro-p-xylene.

46. The process which comprises the steps of
(A) polymerizing to substantially complete conversion at least one first polymerizable olefinically unsaturated monomer under anionic solution polymerization conditions employing a dienyllithium initiator, thereby resulting in a polymerization admixture containing polymer terminated at least in part with a conjugated dienyl functional group, wherein said dienyllithium initiator is a product prepared by contacting at least one hydrocarbon lithium compound $R(Li)_x$ with at least one hydrocarbon 1,4-diolefin in a mixed solvent of saturated hydrocarbon/polar compound, under dienyllithium initiator forming temperature conditions, wherein R is a hydrocarbyl radical of valence x, and x is an integer of 1 to 4; and
(B) treating said polymerization admixture containing polymer terminated at least in part with a conjugated dienyl functional group with an effective amount of at least one polyfunctional coupling agent of at least difunctionality, thereby preparing at least in part a coupled dienyl terminated polymer of increased molecular weight and characterized by conjugated dienyl groups on the extending terminal ends of the coupled polymer.

47. The process which comprises the steps of
(A) polymerizing to substantially complete conversion at least one first polymerizable olefinically unsaturated monomer under anionic solution polymerization conditions employing a dienyllithium initiator, thereby resulting in a polymerization admixture containing polymer terminated at least in part with a conjugated dienyl functional group, wherein said dienyllithium initiator is a product prepared by contacting at least one hydrocarbon lithium compound $R(Li)_x$ with at least one hydrocarbon 1,4-diolefin in a mixed solvent of saturated hydrocarbon/polar compound, under dienyllithium initiator forming temperature conditions, wherein R is a hydrocarbyl radical of valence x, and x is an integer of 1 to 4; and
(B) treating said polymerization admixture containing polymer terminated at least in part with a conjugated dienyl functional group with at least one unsaturated compound selected from the group consisting of alicyclic conjugated trienes and tetraenes, and linear conjugated dienes, thereby providing a polymer containing at least in part terminal conjugated unsaturation at both ends of the polymer chain.

48. The process which comprises the steps of
(A) polymerizing to substantially complete conversion at least one first polymerizable olefinically unsaturated monomer under anionic solution polymerization conditions employing a dienyllithium initiator, thereby resulting in a polymerization admixture containing polymer terminated at least in part with a conjugated dienyl functional group, wherein said dienyllithium initiator is a product prepared by contacting at least one hydrocarbon lithium compound $R(Li)_x$ with at least one hydrocarbon 1,4-diolefin in a mixed solvent of saturated hydrocarbon/polar compound, under dienyllithium initiator forming temperature conditions, wherein R is a hydrocarbyl radical of valence x, and x is an integer of 1 to 4; and
(B) treating said polymerization admixture containing polymer terminated at least in part with a conjugated dienyl functional group with an active hydrogen-containing compound sufficient to terminate active lithium, and thereafter reinitiating polymerization with a hydrocarbon lithium initiator $R(Li)_x$, with or without the further addition of a second said polymerizable monomer the same or different from said first polymerizable monomer, thereby forming a branched polymer with broadened molecular weight.

49. The process which comprises the steps of
(A) polymerizing to substantially complete conversion at least one first polymerizable olefinically unsaturated monomer under anionic solution polymerization conditions employing a dienyllithium initiator, thereby resulting in a polymerization admixture containing polymer terminated at least in part with a conjugated dienyl functional group, wherein said dienyllithium initiator is a product prepared by contacting at least one hydrocarbon lithium compound $R(Li)_x$ with at least one hydrocarbon 1,4-diolefin in a mixed solvent of saturated hydrocarbon/polar compound, under dienyllithium initiator forming temperature conditions, wherein R is a hydrocarbyl radical of valence x, and x is an integer of 1 to 4; and
(B) maintaining said polymerization admixture containing polymer terminated at least in part with a conjugated dienyl functional group at substantially polymerization temperatures for a time sufficient to effect at least partial self-coupling, and thereafter adding a second said polymerizable monomer and polymerizing thereonto, thereby resulting in a branched polymer at least in part.

50. The process which comprises the steps of
(A) polymerizing to substantially complete conversion at least one first polymerizable olefinically unsaturated monomer under anionic solution polymerization conditions employing a dienyllithium initiator, thereby resulting in a polymerization admixture containing polymer terminated at least in part with a conjugated dienyl functional group, wherein said dienyllithium initiator is a product prepared by contacting at least one hydrocarbon lithium compound $R(Li)_x$ with at least one hydrocarbon 1,4-diolefin in a mixed solvent of saturated hydrocarbon/polar compound, under dienyllithium initiator forming temperature conditions, wherein R is a hydrocarbyl radical of valence x, and x is an integer of 1 to 4; and
(B) treating said polymerization admixture containing polymer terminated at least in part with a conjugated dienyl functional group with an effective amount of at least one polyfunctional coupling agent of at least difunctionality, thereby preparing at least in part a coupled conjugated dienyl terminated polymer of increased molecular weight, followed by reinitiating polymerization with a further addition of a hydrocarbon lithium initiator R(Li)$_x$, with or without the further addition of a second said polymerizable olefinically unsaturated monomer the same or different from said first polymerizable monomer, thereby resulting at least in part in a branched polymer.

51. A coupled polymer prepared by steps comprising (A) polymerizing at least one monomer from the group consisting of conjugated dienes, monovinylarenes, acrylates, vinylpyridines, vinylidene halides, and vinylquinolines, under anionic solution polymerization conditions employing a dienyllithium initiator, thereby resulting in a polymer terminated at least in part with a conjugated dienyl functional group, wherein said dienyllithium initiator is a reaction product of at least one hydrocarbon lithium compound R(Li)$_x$ with at least one hydrocarbon 1,4-diolefin in a mixed solvent of saturated hydrocarbon/polar compound, under dienyllithium initiator forming temperature conditions, wherein R has a valence of x and is a hydrocarbyl radical of 1 to 20 carbons wherein x is an integer of 1 to 4, and (B) treating said polymer containing at least in part conjugated dienyl functional group termination with an effective coupling amount of a polyfunctional coupling agent of at least difunctionality, thereby at least in part coupling said conjugated dienyl terminated polymer and resulting in a coupled polymer of increased molecular weight and characterized by conjugated dienyl groups on the extending ends of the coupled polymer.

52. A polymer containing at least in part terminal conjugated unsaturation at each end of the polymer chain prepared by steps comprising (A) polymerizing at least one monomer from the group consisting of conjugated dienes, monovinylarenes, acrylates, vinylpyridines, vinylidene halides, and vinylquinolines, under anionic solution polymerization conditions employing a dienyllithium initiator, thereby resulting in a polymer terminated at least in part with a conjugated dienyl functional group, wherein said dienyllithium initiator is a reaction product of at least one hydrocarbon lithium compound R(Li)$_x$ with at least one hydrocarbon 1,4-diolefin in a mixed solvent of saturated hydrocarbon/polar compound, under dienyllithium initiator forming temperature conditions, wherein R has a valence of x and is a hydrocarbyl radical of 1 to 20 carbons wherein x is an integer of 1 to 4, and (B) treating said polymer containing at least in part conjugated dienyl functional group termination with an unsaturated compound selected from the group consisting of alicyclic conjugated trienes and tetraenes, and linear conjugated dienes, in an amount effective to provide about one mole of said unsaturated compound per equivalent of lithium initiator employed in said (A) thereby providing said polymer containing at least in part terminal conjugated unsaturation at each end of the polymer chain.

53. A branched polymer prepared by steps comprising (A) polymerizing at least one monomer from the group consisting of conjugated dienes, monovinylarenes, acrylates, vinylpyridines, vinylidene halides, and vinylquinolines, under anionic solution polymerization conditions employing a dienyllithium initiator, thereby resulting in a polymer terminated at least in part with a conjugated dienyl functional group, wherein said dienyllithium initiator is a reaction product of at least one hydrocarbon lithium compound R(Li)$_x$ with at least one hydrocarbon 1,4-diolefin in a mixed solvent of saturated hydrocarbon/polar compound, under dienyllithium initiator forming temperature conditions, wherein R has a valence of x and is a hydrocarbyl radical of 1 to 20 carbons wherein x is an integer of 1 to 4, and (B) treating said polymer containing at least in part conjugated dienyl functional group termination with an active hydrogen-containing compound sufficient to terminate active lithium, and thereafter reinitiating polymerization with a hydrocarbon lithium initiator R(Li)$_x$, with or without the further addition of a second said polymerizable monomer the same or different from said first polymerizable monomer, thereby forming a branched polymer with broadened molecular weight.

54. A branched polymer prepared by steps comprising (A) polymerizing at least one monomer from the group consisting of conjugated dienes, monovinylarenes, acrylates, vinylpyridines, vinylidene halides, and vinylquinolines, under anionic solution polymerization conditions employing a dienyllithium initiator, thereby resulting in a polymer terminated at least in part with a conjugated dienyl functional group, wherein said dienyllithium initiator is a reaction product of at least one hydrocarbon lithium compound R(Li)$_x$ with at least one hydrocarbon 1,4-diolefin in a mixed solvent of saturated hydrocarbon/polar compound, under dienyllithium initiator forming temperature conditions, wherein R has a valence of x and is a hydrocarbyl radical of 1 to 20 carbons wherein x is an integer of 1 to 4, and (B) maintaining said polymer containing at least in part conjugated dienyl functional group termination at polymerization temperatures for a time sufficient to effect at least partial self-coupling, and thereafter adding a second said polymerizable monomer and polymerizing thereonto to produce a branched polymer.

55. A branched polymer prepared by the steps comprising (A) polymerizing at least one monomer from the group consisting of conjugated dienes, monovinylarenes, acrylates, vinylpyridines, vinylidene halides, and vinylquinolines, under anionic solution polymerization conditions employing a dienyllithium initiator, thereby resulting in a polymer terminated at least in part with a conjugated dienyl functional group, wherein said dienyllithium initiator is a reaction product of at least one hydrocarbon lithium compound R(Li)$_x$ with at least one hydrocarbon 1,4-diolefin in a mixed solvent of saturated hydrocarbon/polar compound, under dienyllithium initiator forming temperature conditions, wherein R has a valence of x and is a hydrocarbyl radical of 1 to 20 carbons wherein x is an integer of 1 to 4, and (B) treating said polymer containing at least in part conjugated dienyl functional group termination with an effective coupling amount of a polyfunctional coupling agent of at least difunctionality, thereby at least in part coupling said conjugated dienyl terminated polymer, followed by reinitiating polymerization with a hydrocarbon lithium initiator R(Li)$_x$, with or without the further addition of a second polymerizable monomer the same or different from said first polymerizable monomer.

56. A hexadienyl terminated isoprene-styrene-butadiene-styrene-isoprene pentablock copolymer prepared by the steps which comprise (A) polymerization of isoprene, sequentially followed by polymerization of styrene, sequentially followed by polymerization of 1,3-butadiene, under anionic solution polymerization conditions employing a dienyllithium initiator, thereby resulting in a polymer terminated at least in part with a conjugated dienyl functional group, wherein said dienyllithium initiator is a reaction product of at least one hydrocarbon lithium compound $R(Li)_x$ with at least one hydrocarbon 1,4-diolefin in a mixed solvent of saturated hydrocarbon/polar compound, under dienyllithium initiator forming temperature conditions, wherein R has a valence of x and is a hydrocarbyl radical of 1 to 20 carbons wherein x is an integer of 1 to 4, and (B) thereafter treating said polymer containing at least in part conjugated dienyl functional group termination with an effective coupling amount of a polyfunctional coupling agent of at least difunctionality, thereby at least in part coupling said conjugated dienyl terminated polymer and resulting in a coupled polymer of increased molecular weight and characterized by conjugated dienyl groups on the extending ends of the coupled polymer, and thereafter terminating any remaining active lithium.

57. The pentablock copolymer as defined by claim 56 wherein said step (A) employs hexadienyllithium as said dienyllithium initiator, and said (B) employs a polyfunctional treating agent which is $\alpha,\alpha'$-dichloro-p-xylene.

* * * * *